(12) United States Patent  (10) Patent No.: US 8,462,340 B2
Obata  (45) Date of Patent: Jun. 11, 2013

(54) GEL PARTICLE MEASURING APPARATUS

(76) Inventor: Toru Obata, Tokyo (JP)

( * ) Notice: Subject to any disclaimer, the term of this patent is extended or adjusted under 35 U.S.C. 154(b) by 342 days.

(21) Appl. No.: 12/933,330

(22) PCT Filed: Mar. 19, 2009

(86) PCT No.: PCT/JP2009/055472
 § 371 (c)(1),
 (2), (4) Date: Sep. 17, 2010

(87) PCT Pub. No.: WO2009/116633
 PCT Pub. Date: Sep. 24, 2009

(65) Prior Publication Data
 US 2011/0013185 A1    Jan. 20, 2011

(30) Foreign Application Priority Data
 Mar. 19, 2008 (JP) ................................ 2008-071328

(51) Int. Cl.
 *G01N 21/00* (2006.01)
(52) U.S. Cl.
 USPC ........................................................ 356/338
(58) Field of Classification Search
 USPC ................................................ 356/338, 432
 See application file for complete search history.

(56) References Cited

U.S. PATENT DOCUMENTS

| 4,843,021 | A | * | 6/1989 | Noguchi et al. | ............... | 436/533 |
| 5,100,805 | A | * | 3/1992 | Ziege et al. | ................... | 436/517 |
| 5,494,800 | A | | 2/1996 | Smith, III | | |
| 5,715,173 | A | * | 2/1998 | Nakajima et al. | ............. | 700/266 |
| 5,907,399 | A | | 5/1999 | Shirasawa et al. | | |
| 2010/0129260 | A1 | * | 5/2010 | Shirasawa | ................... | 422/82.05 |
| 2010/0178206 | A1 | * | 7/2010 | Obata et al. | ...................... | 422/73 |

FOREIGN PATENT DOCUMENTS

| CN | 6898817 | Y | 5/2007 |
| EP | 0 350 273 | A2 | 1/1990 |
| JP | 61-93958 | A | 5/1986 |
| JP | 61-159162 | A | 7/1986 |
| JP | 2-74864 | A | 3/1990 |
| JP | 6-50875 | A | 2/1994 |

(Continued)

OTHER PUBLICATIONS

Obata et al., "Early detection of the Limulus amebocyte lysate reaction evoked by endotokins," Analytical Biochemistry (2008), vol. 373, pp. .281-286.

(Continued)

*Primary Examiner* — Roy M Punnoose
(74) *Attorney, Agent, or Firm* — Birch, Stewart, Kolasch & Birch, LLP

(57) ABSTRACT

A gel particle measuring apparatus detects a gel particle production starting point with high sensitivity, for measurement of a target substance in a sample by a gelation reaction. The gel particle measuring apparatus includes a sample cell accommodating a sample and a solution containing a reagent, a stirring device for stirring a mixed solution including the sample and the solution containing the reagent, a coherent light source that irradiates the mixed solution with coherent light, a transmitted light detecting device outside the sample cell, on the opposite side of the coherent light source, a transmitted light fluctuation detecting device for detecting a fluctuation component of the transmitted light, and a gel particle production determining device for determining at least the production state of gel particles, which leads to timing of phase transition of the mixed solution from a sol phase to a gel phase.

13 Claims, 14 Drawing Sheets

FOREIGN PATENT DOCUMENTS

| | | |
|---|---|---|
| JP | 8-101198 A | 4/1996 |
| JP | 3199850 B2 | 8/2001 |
| JP | 2001-318054 A | 11/2001 |
| JP | 2003-322655 A | 11/2003 |
| JP | 2004-93536 A | 3/2004 |
| JP | 2004-212120 A | 7/2004 |
| JP | 2006-122579 A | 5/2006 |
| JP | 3814559 B2 | 8/2006 |
| JP | 4014310 B2 | 11/2007 |
| WO | WO 2008/038329 A1 | 4/2008 |
| WO | WO 2008/139544 A1 | 11/2008 |

OTHER PUBLICATIONS

Ong et al., "A rapid highly-sensitive endotoxin detection system," Biosensors and Bioelectronics (2006), vol. 21, pp. 2270-2274.

Supplementary European Search Report dated Sep. 13, 2011, issued in European Patent Application No. 09721684.

International Search report dated May 12, 2009 for corresponding PCT/JP2009/055472.

* cited by examiner

FIG.2
(a)
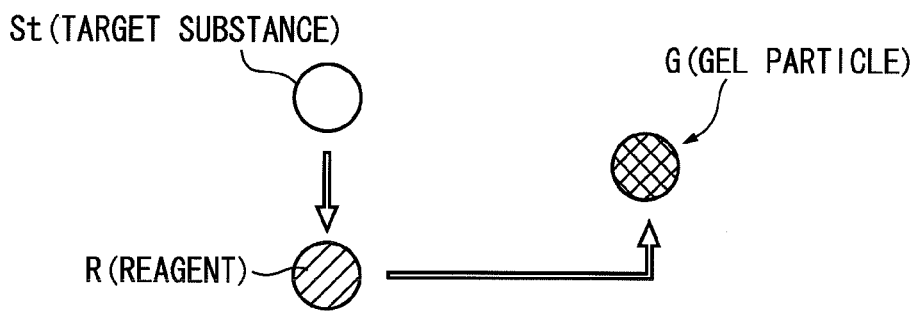
(b)
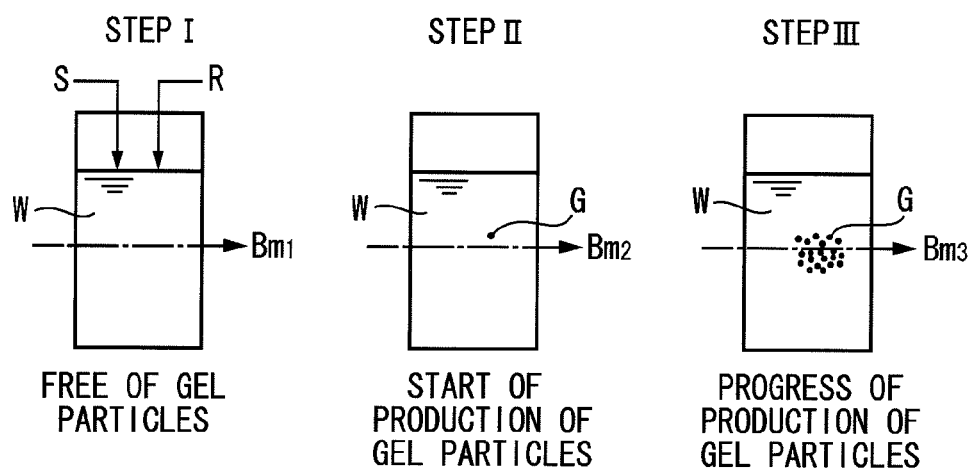
(c)
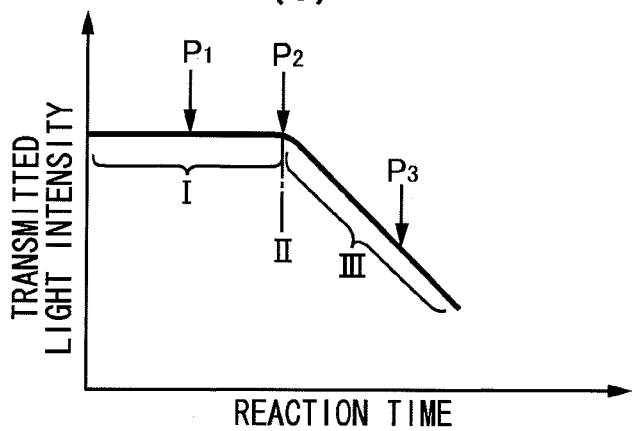

FIG.4
(a)
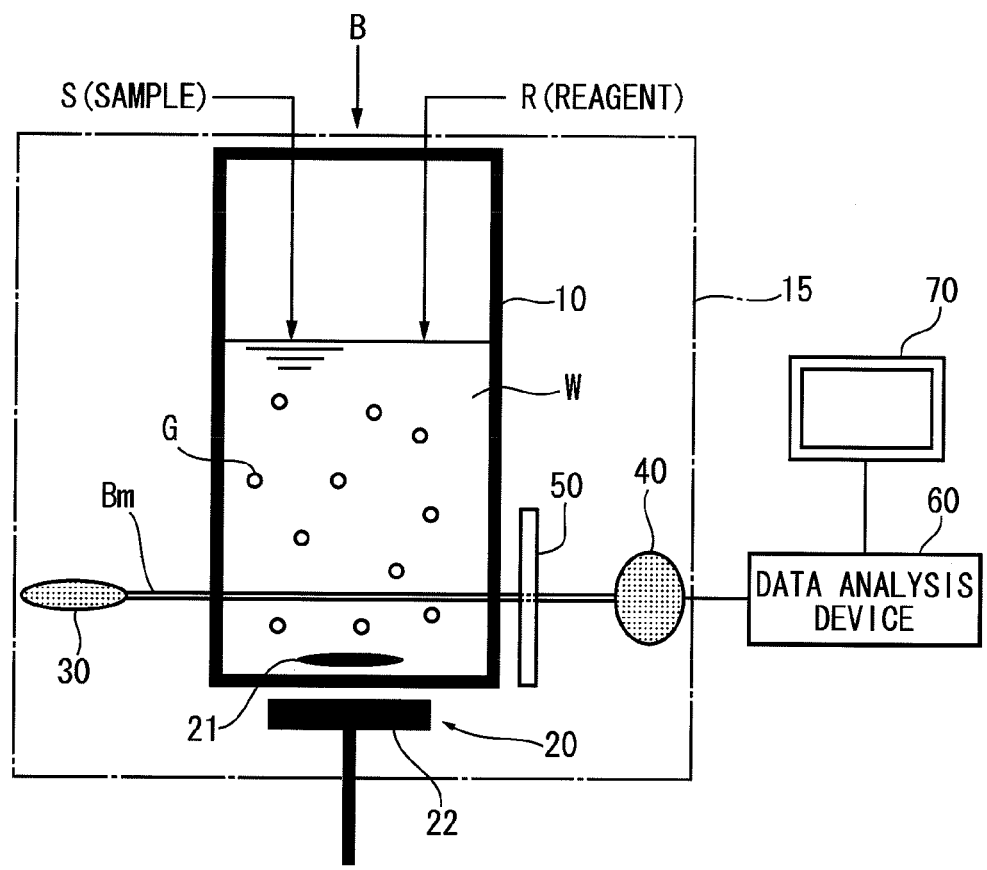
(b)
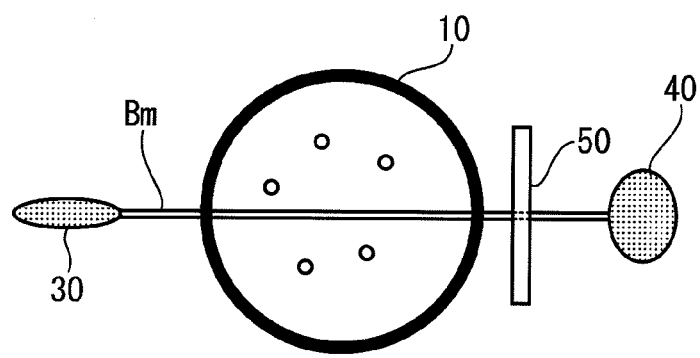

FIG.6
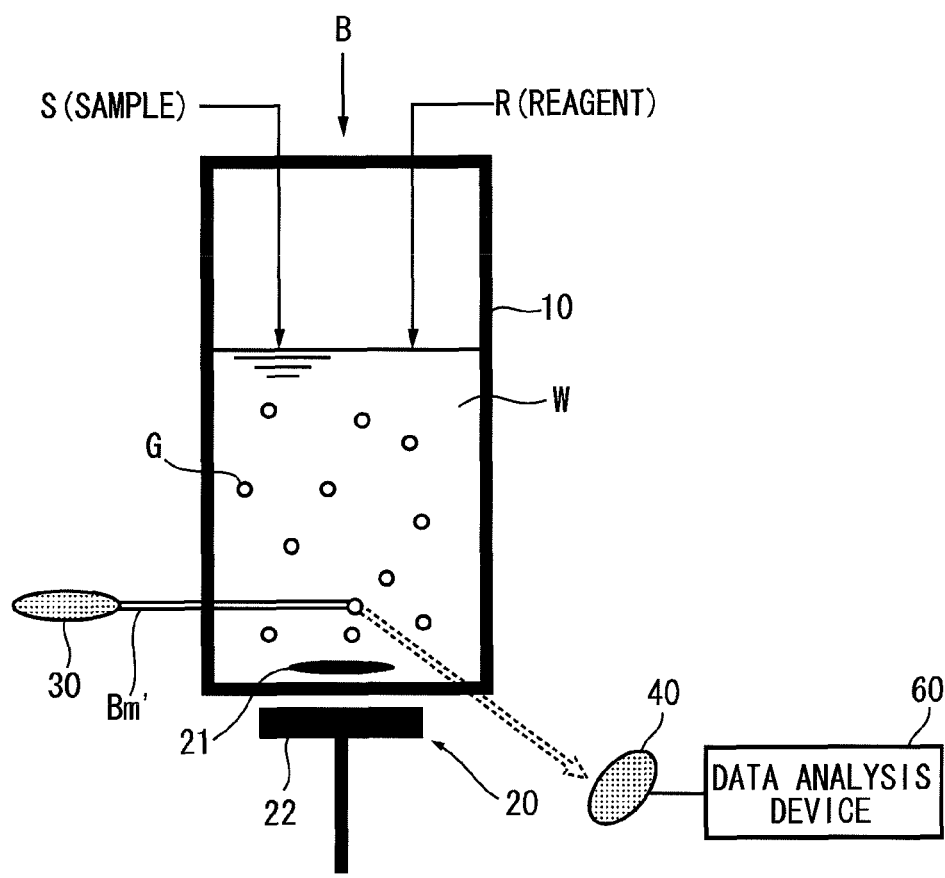
(a)
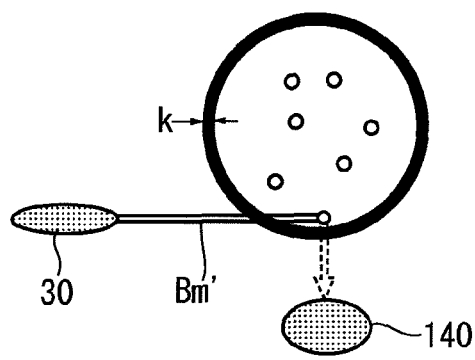
(b)

FIG.7
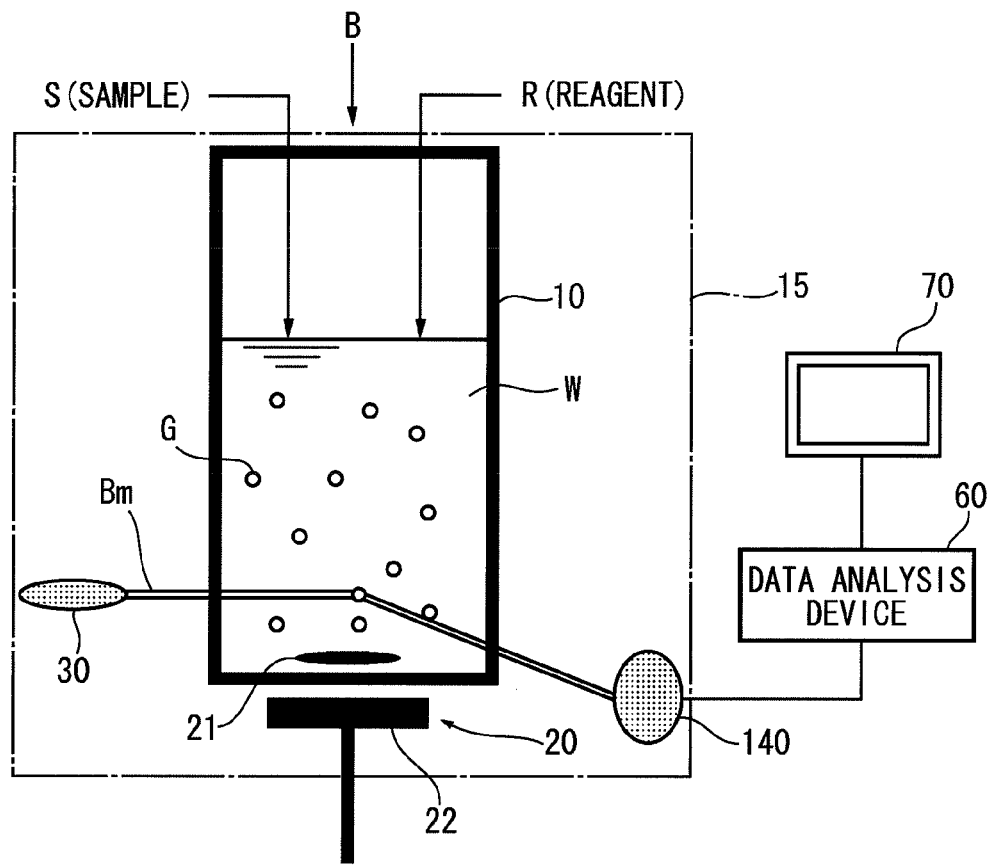
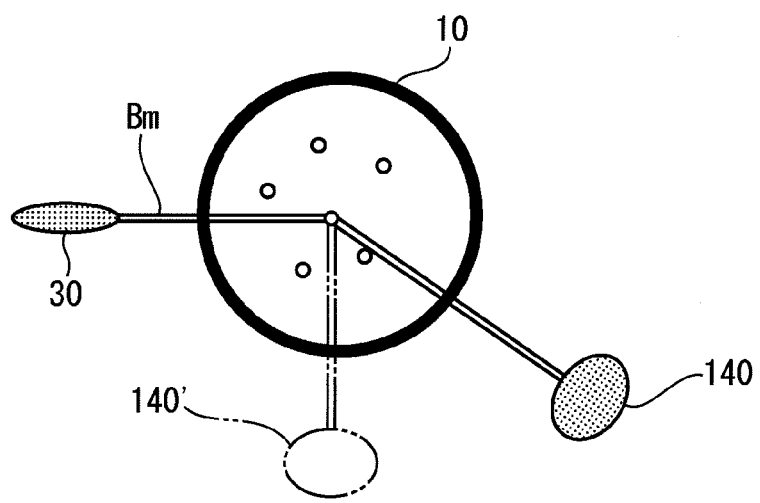

FIG.8
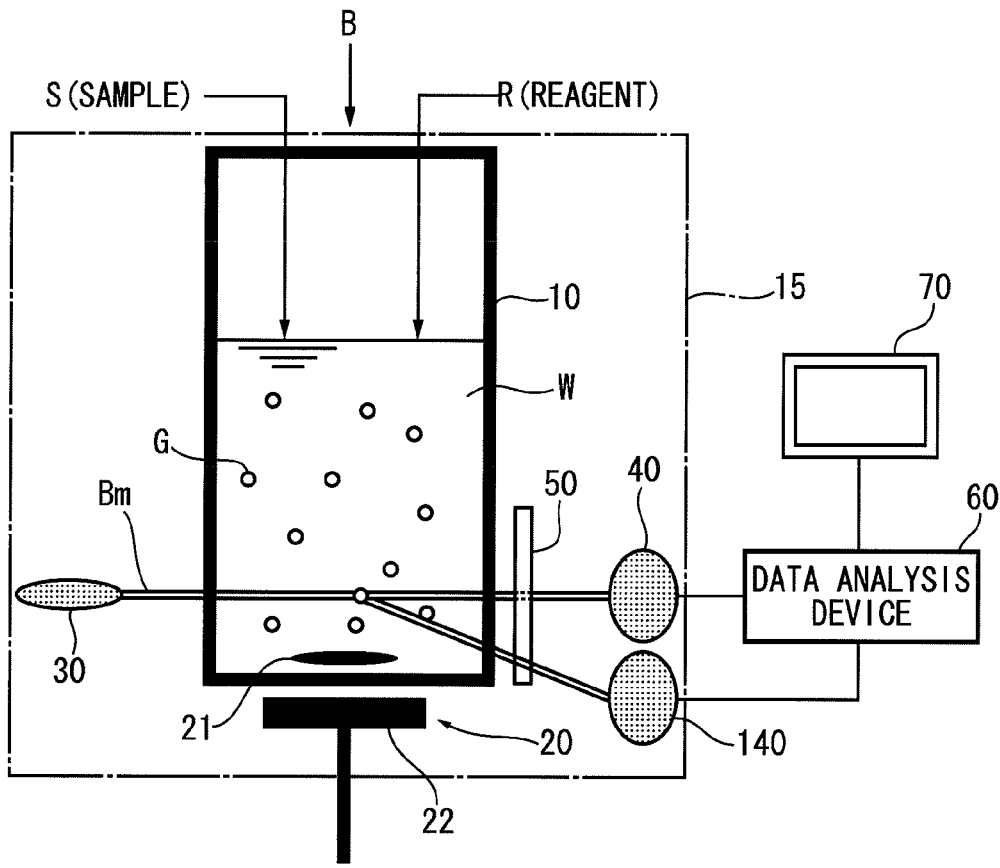
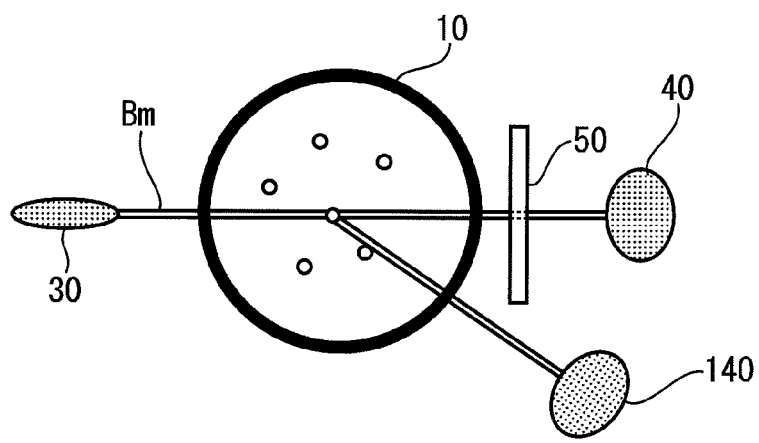

FIG.11
(a)
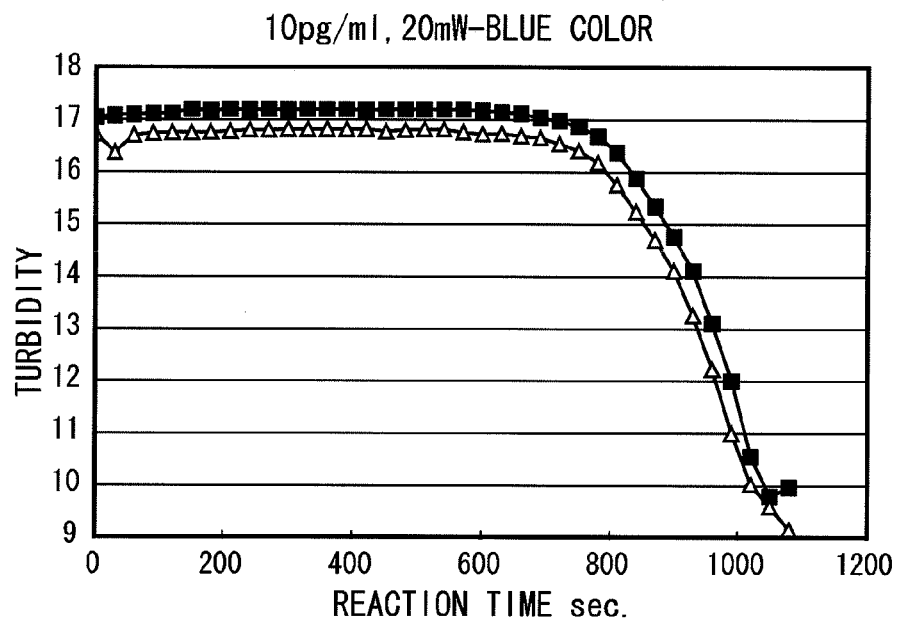
(b)
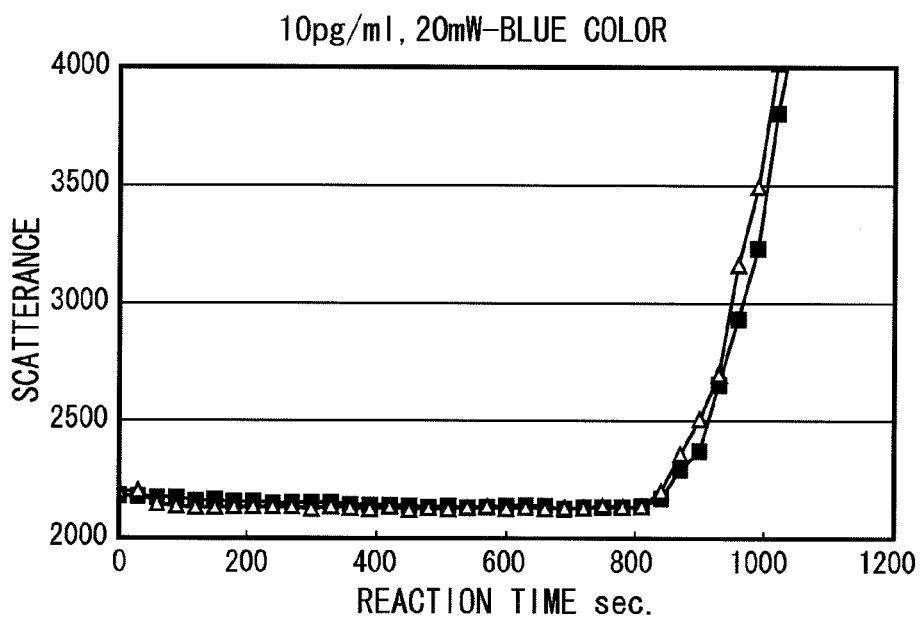

FIG.12
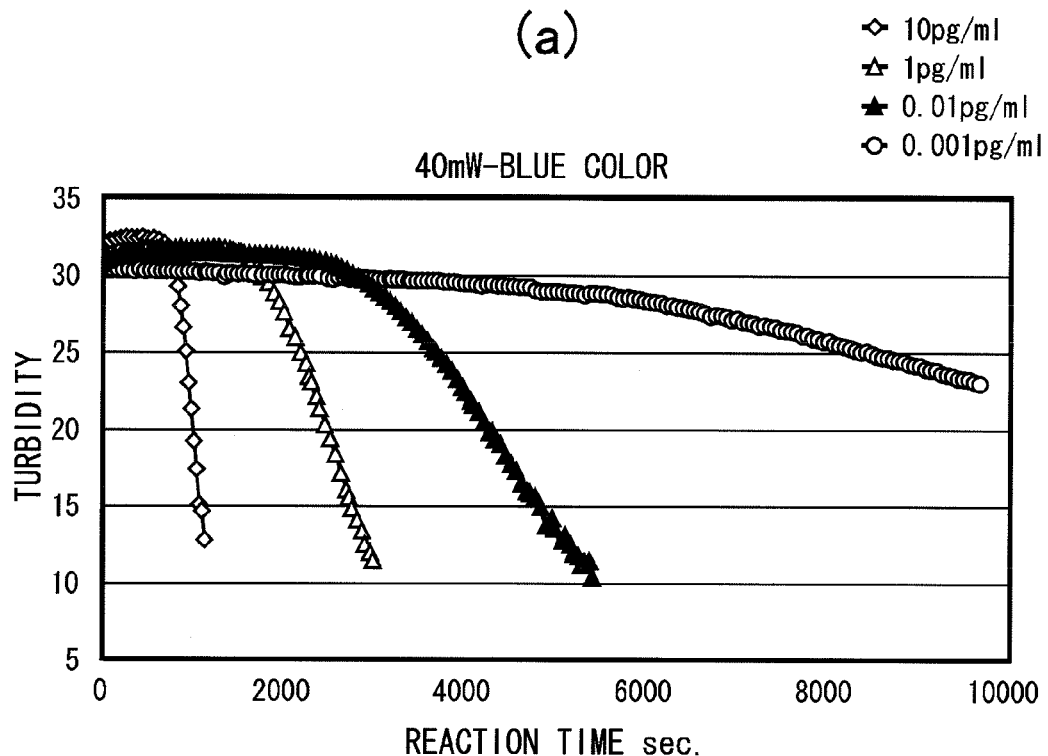
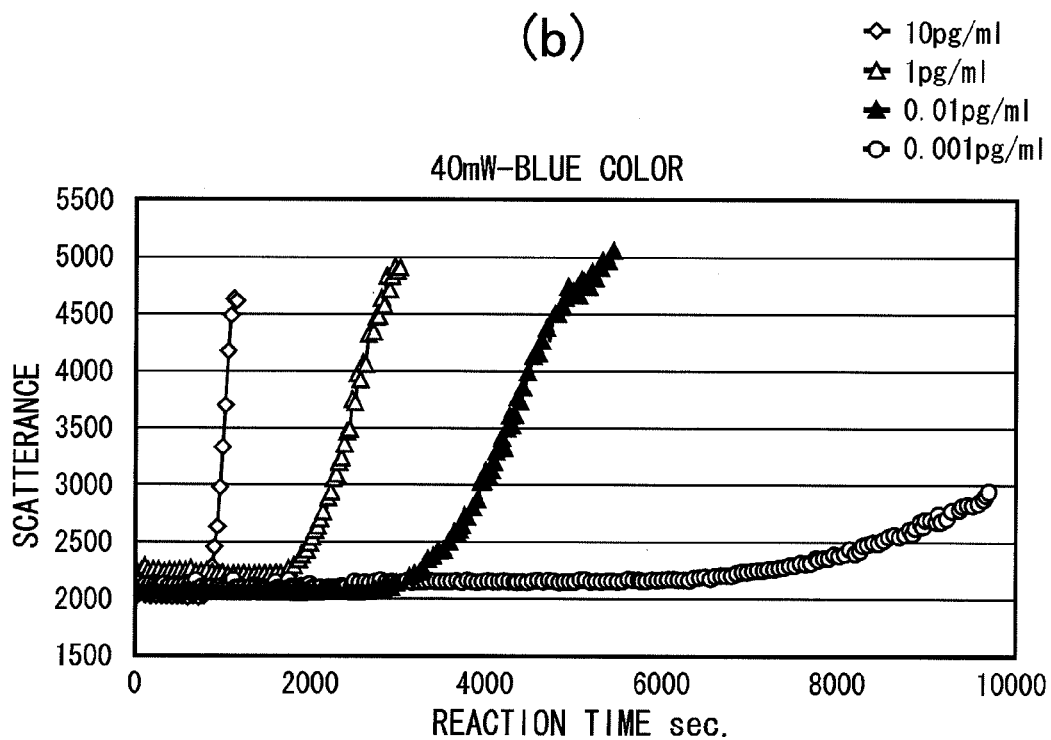

FIG.13
(a)
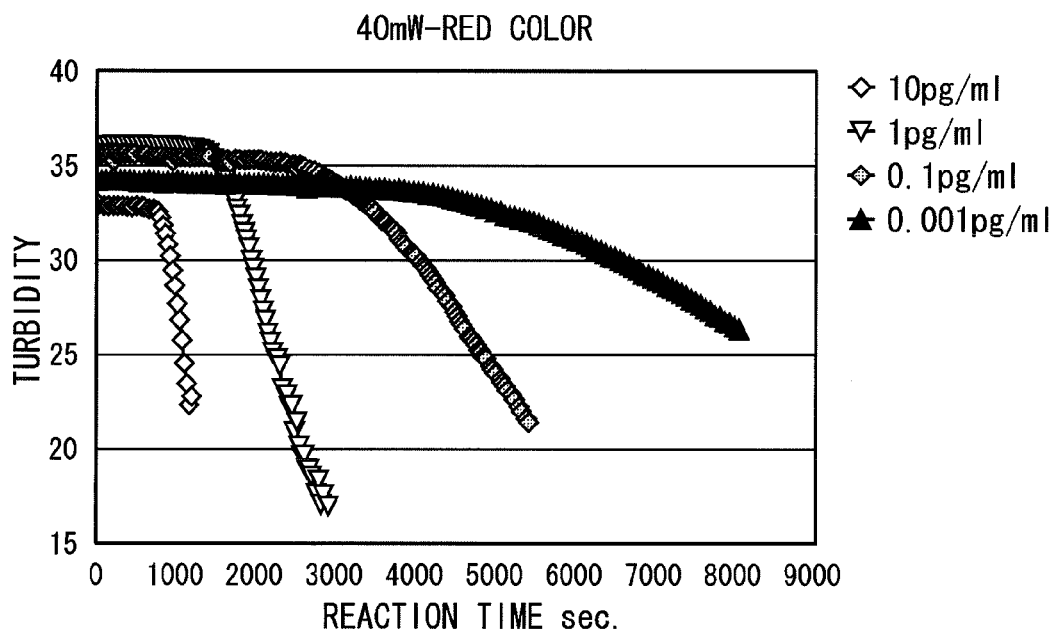
(b)
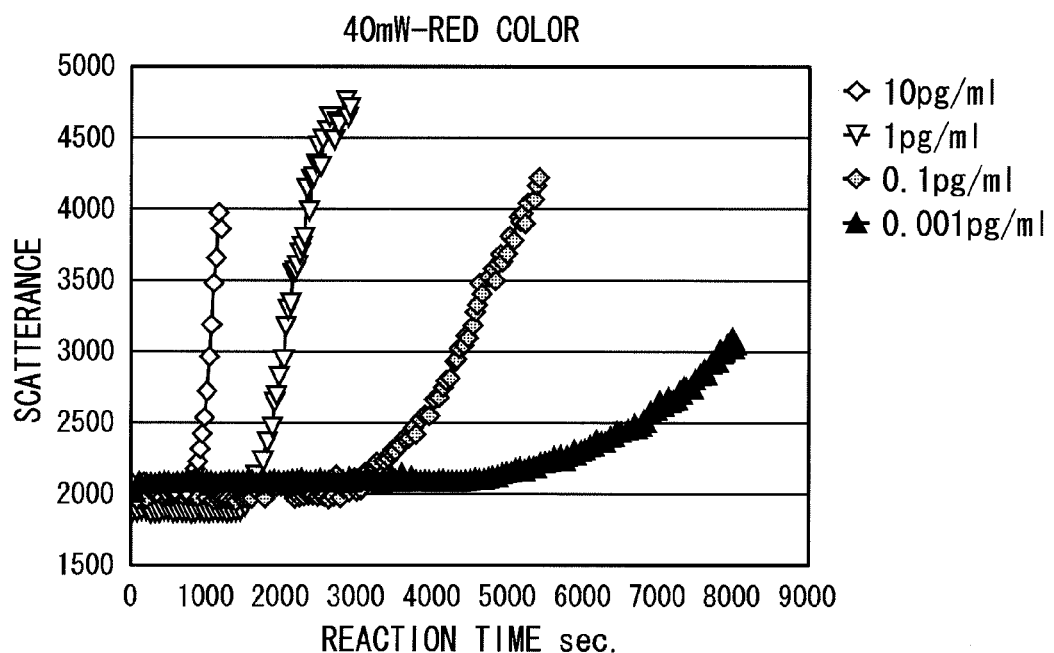

GEL PARTICLE MEASURING APPARATUS

TECHNICAL FIELD

The present invention relates to a gel particle measuring apparatus for detecting particles produced from a target substance such as an endotoxin or a β-D-glucan in a sample as a measuring object by a gelation reaction.

BACKGROUND ART

So-called endotoxins (intracellular toxins) mainly include fragments of cells of bacteria that are not stained by Gram staining (Gram-negative), and a component of the fragments is a lipid-polysaccharide called a lipopolysaccharide. To be specific, the component is a lipopolysaccharide (LPS) in which a lipid called Lipid A and a polysaccharide chain are bonded via 2-keto-3-deoxyoctonate (KDO). A lipid component called Lipid A included in the lipopolysaccharide is bonded to a cellular receptor, causing inflammation, and causing a variety of severe clinical symptoms in many cases. The endotoxins are, as described above, substances causing clinical symptoms such as sepsis and bacteremia that are high in fatality. Thus, estimation of the endotoxins present in the body is highly demanded clinically.

Further, it is important that medicinal products (such as injections) and medical devices (such as angiocatheters) are free of endotoxin contamination (pyrogen-free), and it is strictly required that endotoxins be completely removed from medicinal products (such as recombinant proteins and DNA used for gene therapies) prepared by using bacteria.

In confirmation of the removal of endotoxins or measurement of endotoxins in emergency medicine, promptness is required for attaining the purposes of coping with a large number of measuring samples and carrying out life-saving treatment.

Research has been made since old days on measuring the value of endotoxins for the treatment of sepsis or the like. Since the discovery of a fact that a factor group contained in the component of an amebocyte of a horseshoe crab (*Limulus polyphemus*) specifically reacts with endotoxins, resulting in gelation, trials for quantifying the endotoxins have been made by using *limulus* amebocyte lysates (LAL reagent or *limulus* reagent).

A measuring method in which the *limulus* reagent was used for the first time was a simple measuring method called a gelation method, in which plasma from a patient serving as a sample is mixed with the *limulus* reagent, the mixture is left to stand still, the mixture is positioned up side down after a certain time, the presence or absence of gelation is confirmed by whether or not the solution is solidified, and the amount of endotoxins is estimated based on the maximum dilution ratio at which the gelation is caused.

Later, attention has been paid to the increase of turbidity during a gelation reaction. As a result, there is known a turbidimetric time assay, in which a turbidimeter using an optical measuring method is used to measure an endotoxin concentration based on changes in turbidity involved in the gelation reaction.

In addition, a synthetic chromogenic substrate method has already been known, in which method a gelation reaction causing a conversion from coagulogen to coagulin is replaced by a chromogenic reaction of a synthetic substrate in the final stage of a reaction process caused by a *limulus* reagent. This is a method in which a synthetic chromogenic substrate (Boc-Leu-Gly-Arg-p-nitroanilide) is added in place of a coagulation precursor (coagulogen) in a coagulation process, the hydrolysis of the synthetic chromogenic substrate then produces free p-nitroaniline, and the colorimetric analysis of the resultant yellow chromogenic development is performed to measure an endotoxin concentration.

Besides, the following measuring apparatuses disclosed in Patent Documents 1 and 2 are exemplified as a conventional gelation-reaction measuring apparatus or a measuring apparatus associated with the conventional gelation-reaction measuring apparatus.

Patent Document 1 does not relate to a gelation-reaction measuring apparatus, but relates to a method of measuring the size and number of the aggregated clumps of platelets in blood at each of the processes in which the platelets aggregate and grow as clumps. This is a method in which a sample in a sample cell is irradiated with an illuminating radiation from a laser light source, the scattered light that has been scattered laterally by 90° because of the presence of the platelets is partially detected with a photodetector, and the size and number of the aggregated clumps of the platelets are measured based on the detection results.

Further, Patent Document 2 relates to a gelation-reaction measuring apparatus using a turbidimetric time assay. This is an assay in which the time-dependent changes of the intensity of transmitted light in a mixed solution obtained by mixing a specimen (sample) and a limulus reagent are measured, and an endotoxin concentration in the specimen is measured based on the amounts of the changes in a predetermined time.

Moreover, measuring techniques using a gelation reaction are used for measuring not only the endotoxins described above but also β-D-glucans or the like.

β-D-glucans are polysaccharides constituting cell membranes specific to fungi. Measurement of the β-D-glucans is effective for screening a wide variety of fungi responsible for fungal infection, including not only fungi found in a general clinical environment, such as *Candida*, *Aspergillus*, or *Cryptococcus*, but also fungi rarely found in the general clinical environment.

The phenomenon in which a component extracted from a amebocyte of a *limulus* is gelated with β-D-glucans is also used in the measurement of β-D-glucans, and the above-mentioned gelation method, turbidimetric time assay, or synthetic chromogenic substrate method is used to carry out the measurement.

Measuring techniques of endotoxins and of β-D-glucans have common points. For example, almost the same kind of measuring hardware is used to remove a Factor G component from the components extracted from amebocyte of *Limulus*, and hence a gelation reaction or chromogenic reaction selective to endotoxins can be measured. Alternatively, endotoxins in a sample are inactivated by pretreatment, and hence a gelation reaction or chromogenic reaction selective to β-D-glucans can be measured.

Patent Document 1: JP 3199850 B2 (Examples and FIG. 1)
Patent Document 2: JP 2004-93536 A (Modes for carrying out the Invention and FIG. 3)

DISCLOSURE OF THE INVENTION

Problems to be Solved by the Invention

However, the gelation method, turbidimetric time assay, and synthetic chromogenic substrate method, all of which have been conventionally used, have the following drawbacks.

Both the gelation method and the turbidimetric time assay need as long a time as about 90 minutes or longer under low concentrations for the production of gels to take place. That is, although the gelation time of a reaction solution is proportional to the concentration of a target substance in a sample as a measuring object, it is not possible to detect the accurate starting time of gelation or the like by both the gelation method and the turbidimetric time assay because of inferior sensitivity, and hence a reaction amount is calculated based on the time until the completion of the gelation, and the reaction amount serves as an indication for the gelation time.

The turbidimetric time assay is taken as an example. By using the turbidimetric time assay, it is possible to identify the initial turbidity level at which a change starts and the level at which the change arrives, but it is hard to identify the time at which each change starts and the time at which the each change finishes. Thus, the turbidimetric time assay has been established as a quantification method in which measurement of a change at a certain level (increase in turbidity) between the initial level and the final level is carried out instead of the observation of a change in whole gelation. However, when the concentration of endotoxins is low, the gelation of the whole system is delayed, and at the same time, a change in turbidity to be observed is expanded, resulting in a difficulty in measuring the change in turbidity. As a result, sensitivity inevitably declines.

Thus, it is hard to say that both the gelation method and the turbidimetric time assay are suitable for the case where emergency is required and for the measurement of many specimens. Besides, when the turbidimetric time assay is carried out, unspecific turbidity irrelevant to endotoxins occurs in some cases, and hence the turbidimetric time assay may lack measurement accuracy. Moreover, the critical concentration for measurement in the gelation method is 3 pg/ml, and the critical concentration for measurement in the turbidimetric time assay is about 1 pg/ml.

Note that even if the scattering photometry disclosed in Patent Document 1 is applied as a turbidimetric time assay applied to a gelation-reaction measuring apparatus, the scattering photometry is a quantification method in which the observation of the change in whole gelation is not carried out, and hence the above-mentioned problems cannot be solved.

On the other hand, the measurement time of the synthetic chromogenic substrate method is as short as about 30 minutes compared with those of the gelation method and turbidimetric time assay. However, because a false-positive reaction occurs in some cases, the synthetic chromogenic substrate method has a difficulty in carrying out measurement with high specificity. Besides, in the synthetic chromogenic substrate method, preparation for measurement is troublesome, and the critical concentration for measurement is 3 pg/ml, which is inferior to the turbidimetric time assay.

The present invention provides a gel particle measuring apparatus for detecting with high sensitivity the production state of gel particles, which leads to the timing of phase transition of a mixed solution including a sample and a solution containing a reagent from a sol phase to a gel phase, when a target substance in the sample is measured through a gelation reaction.

Means for Solving the Problems

The invention according to claim 1 is a gel particle measuring apparatus for detecting particles produced from a target substance in a sample by a gelation reaction, the apparatus including: a sample cell that has at least a transmission portion through which light transmits from one side to the other side and that accommodates a sample containing a target substance as a measuring object and a solution containing a reagent causing gelation of the target substance; stirring means for stirring a mixed solution including the sample and the solution containing the reagent in the sample cell so as to inhibit gelation of the mixed solution constantly as a whole; a coherent light source that is provided outside the transmission portion of the sample cell and irradiates the mixed solution including the sample and the solution containing the reagent in the sample cell with coherent light; transmitted light detecting means that is provided at a position outside the transmission portion of the sample cell and on the opposite side of the coherent light source and that is used for detecting transmitted light through the mixed solution including the sample and the solution containing the reagent in the sample cell; transmitted light fluctuation measuring means for measuring a fluctuation component of the transmitted light based on the detection output of the transmitted light detecting means; and gel particle production determining means for determining at least the production state of gel particles in the mixed solution, which leads to timing of phase transition of the mixed solution from a sol phase to a gel phase, based on the results of measurement of the transmitted light fluctuation measuring means.

The invention according to claim 2 is a gel particle measuring apparatus according to claim 1, further including scattered light removing means for removing a component travelling toward the transmitted light detecting means out of phase-shifted scattered light scattered by gel particles, between the transmitted light detecting means and the sample cell.

The invention according to claim 3 is a gel particle measuring apparatus according to claim 1 or 2, in which the gel particle production determining means includes means for determining a changing point, at which the fluctuation displacement of the transmitted light changes from a stable state to an unstable state, as emerging timing of the gel particles, based on the results of measurement of the transmitted light fluctuation measuring means.

The invention according to claim 4 is a gel particle measuring apparatus according to any one of claims 1 to 3, in which the coherent light source includes a laser light source.

The invention according to claim 5 is a gel particle measuring apparatus according to any one of claims 1 to 4, in which the sample cell includes, in a cell container, the stirring means with which the sample and the solution containing the reagent can be directly stirred constantly.

The invention according to claim 6 is a gel particle measuring apparatus according to any one of claims 1 to 5, in which the sample cell is provided in a thermostatic chamber.

The invention according to claim 7 is a gel particle measuring apparatus according to any one of claims 1 to 6, further including display means for displaying the results of determination by the gel particle production determining means.

The invention according to claim 8 is a gel particle measuring apparatus according to any one of claims 1 to 7, in which the gel particle production determining means includes means for quantifying the target substance in the sample based on the production state of the gel particles.

The invention according to claim 9 is a gel particle measuring apparatus for measuring particles produced from a target substance in a sample by a gelation reaction, the apparatus including: a sample cell that has at least a transmission portion through which light transmits and that accommodates a sample containing a target substance as a measuring object and a solution containing a reagent causing gelation of the target substance; stirring means for stirring a mixed solution including the sample and the solution containing the reagent in the sample cell so as to inhibit gelation of the mixed solution as a whole; a coherent light source that is provided outside the transmission portion of the sample cell and irradiates the mixed solution including the sample and the solution containing the reagent in the sample cell with coherent light; passing light detecting means that is provided at a position outside the transmission portion of the sample cell, the position being different from a position at which the coherent light source is provided, and that is used for detecting passing light through the mixed solution including the sample and the solution containing the reagent in the sample cell; passing light fluctuation measuring means for measuring a fluctuation component of the passing light based on a detection output of the passing light detecting means; and gel particle production determining means for determining at least the production state of gel particles in the mixed solution, which leads to timing of phase transition of the mixed solution from a sol phase to a gel phase, based on the results of measurement of the passing light fluctuation detecting means.

The invention according to claim 10 is a gel particle measuring apparatus according to claim 9, in which the gel particle production determining means includes means for determining a changing point, at which the fluctuation displacement of the passing light changes from a stable state to an unstable state, as emerging timing of the gel particles, based on the results of measurement of the passing light fluctuation measuring means.

The invention according to claim 11 is a gel particle measuring apparatus according to claim 9, in which the coherent light source irradiates the mixed solution with coherent light so that the coherent light passes near the center of the sample cell, and the passing light detecting means includes means for detecting scattered light out of light from the coherent light source, the light passing through the mixed solution in the sample cell.

The invention according to claim 12 is a gel particle measuring apparatus according to claim 9, in which the coherent light source irradiates the mixed solution with coherent light so that the coherent light passes near the center of the sample cell, and the passing light detecting means includes means for detecting transmitted light and scattered light out of light from the coherent light source, the light passing through the mixed solution in the sample cell.

The invention according to claim 13 is a gel particle measuring apparatus according to any one of claims 1 to 12, in which the target substance as the measuring object includes an endotoxin and the reagent for gelating the endotoxin includes a limulus reagent.

Effects of the Invention

According to the invention according to claim 1, there can be detected with high sensitivity the production state of the gel particles, which corresponds to the timing of phase transition of the mixed solution including the sample and the solution containing the reagent from a sol phase to a gel phase, based on the fluctuation component of the transmitted light transmitting through the mixed solution, when the target substance in the sample is measured through the gelation reaction.

According to the invention according to claim 2, detection accuracy with the transmitted light detecting means can be further enhanced, and hence there can be detected with high sensitivity the production state of the gel particles, indicating the phase transition of the mixed solution from the sol phase to the gel phase.

According to the invention according to claim 3, the concentration of the target substance in the sample by can be promptly quantified by determining the emerging timing of the gel particles.

According to the invention according to claim 4, the coherent light source can be easily provided.

According to the invention according to claim 5, the mixed solution including the sample and the solution containing the reagent can be stirred more surely, and hence the production condition of the gel particles can be satisfied.

According to the invention according to claim 6, the gelation reaction can be stably progressed under a thermostatic environment.

According to the invention according to claim 7, the results of determination by the gel particle production determining means can be visually observed.

According to the invention according to claim 8, the production of the target substance in the sample can be directly quantified.

According to the invention according to claim 9, there can be detected with high sensitivity the production state of the gel particles, which leads to the timing of phase transition of the mixed solution including the sample and the solution containing the reagent from the sol phase to the gel phase, based on the fluctuation component of the passing light passing through the mixed solution, when the target substance in the sample is measured through the gelation reaction.

According to the invention according to claim 10, there can be detected with high sensitivity the emerging timing of the gel particles, when the target substance in the sample is measured through the gelation reaction.

According to the invention according to claim 11, there can be detected with high sensitivity the production state of the gel particles, which leads to the timing of phase transition of the mixed solution from the sol phase to the gel phase, based on the fluctuation component of the scattered light passing through the mixed solution in the sample cell.

According to the invention according to claim 12, there can be measured with high sensitivity the production state of the gel particles, which leads to the timing of phase transition of the mixed solution from the sol phase to the gel phase, based on the fluctuation components of the transmitted light and the scattered light passing through the mixed solution in the sample cell.

According to the invention according to claim 13, the gel particle measuring apparatus can be applied to the quantification of the endotoxin as the target substance in the sample.

BRIEF DESCRIPTION OF THE DRAWINGS

FIG. 2(a) is an explanatory diagram schematically illustrating a gelation reaction. FIG. 2(b) is an explanatory diagram illustrating progressing steps I to III of the gelation reaction. FIG. 2(c) is an explanatory diagram illustrating a relationship between a reaction time and a transmitted light intensity during the progressing steps of the gelation reaction.

FIG. 4(a) is a front explanatory diagram of a gel particle measuring apparatus according to Embodiment 1. FIG. 4(b) is a plan explanatory diagram of the gel particle measuring apparatus according to Embodiment 1.

FIG. 6 are explanatory diagrams each illustrating one example of a gel particle measuring apparatus according to Embodiment 2.

FIG. 7 are explanatory diagrams each illustrating one example of a gel particle measuring apparatus according to Embodiment 3.

FIG. 8 are explanatory diagrams each illustrating one example of a gel particle measuring apparatus according to Embodiment 4.

FIG. 11($a$) is a graph illustrating results obtained by measuring twice a turbidity corresponding to a transmitted light intensity for each reaction time at a predetermined endotoxin concentration (ETX concentration) by using a gel particle measuring apparatus according to Example 2. FIG. 11($b$) is a graph illustrating results obtained by measuring twice a degree of the scattering corresponding to a scattered light intensity for each reaction time at the predetermined ETX concentration by using the same apparatus.

FIG. 12($a$) is a graph illustrating results obtained by measuring a turbidity corresponding to a transmitted light intensity for each reaction time at various endotoxin concentrations (ETX concentrations) by using a gel particle measuring apparatus according to Example 3. FIG. 12($b$) is a graph illustrating results obtained by measuring a degree of the scattering corresponding to a scattered light intensity for each reaction time at various ETX concentrations by using the same apparatus.

FIG. 13($a$) is a graph illustrating results obtained by measuring a turbidity corresponding to a transmitted light intensity for each reaction time at various endotoxin concentrations (ETX concentrations) by using a gel particle measuring apparatus according to Example 4. FIG. 13($b$) is a graph illustrating results obtained by measuring a degree of the scattering corresponding to a scattered light intensity for each reaction time at various ETX concentrations by using the same apparatus.

DESCRIPTION OF SYMBOLS

1 . . . sample cell, 2 . . . stirring means, 3 . . . coherent light source, 4 . . . transmitted light detecting means, 5 . . . transmitted light fluctuation measuring means, 6 . . . gel particle production determining means, 7 . . . scattered light removing means, 8 . . . thermostatic chamber, 9 . . . display means, S . . . sample, R . . . reagent, W . . . mixed solution, Bm . . . light

BEST MODES FOR CARRYING OUT THE INVENTION

Outline of Embodiments

Figure 1:
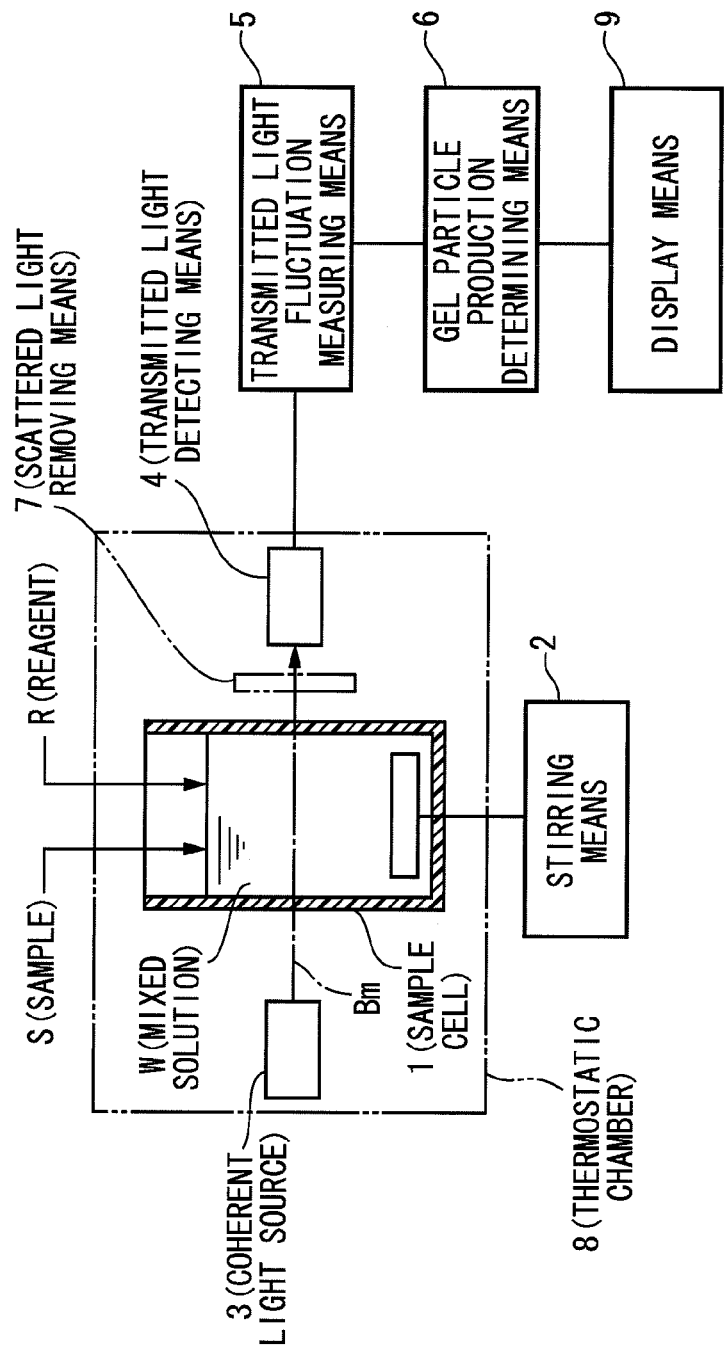
FIG. 1 is an explanatory diagram illustrating an outline of embodiments of a gel particle measuring apparatus to which the present invention is applied.

FIG. 1 is an explanatory diagram illustrating an outline of a gel particle measuring apparatus according to embodiments to which the present invention is applied.

In the diagram, the gel particle measuring apparatus is one that is used for measuring a particle produced by subjecting a target substance in a sample S to a gelation reaction, and the gel particle measuring apparatus includes: a sample cell 1 that has at least a transmission portion through which light transmits from one side to the other side and that contains the sample S containing the target substance as a measuring object and a solution containing a reagent R for causing gelation of the target substance; stirring means 2 for stirring a mixed solution W including the sample S and the solution containing the reagent R in the sample cell 1 so as to disturb gelation of the mixed solution W as a whole; a coherent light source 3 that is provided outside the transmission portion of the sample cell 1 and irradiates the mixed solution W including the sample S and the solution containing the reagent R in the sample cell 1 with coherent light Bm; transmitted light detecting means 4 that is provided at a position outside the transmission portion of the sample cell 1 and on the opposite side of the coherent light source 3 and that is used for detecting the light Bm which has transmitted through the mixed solution W including the sample S and the solution containing the reagent R in the sample cell 1; transmitted light fluctuation measuring means 5 for measuring a fluctuation component of the transmitted light based on the detection output of the transmitted light detecting means 4; and gel particle production determining means 6 for determining at least the production state of gel particles in the mixed solution W, which leads to the timing of phase transition of the mixed solution W from a sol phase to a gel phase, based on the result of measurement by the transmitted light fluctuation measuring means 5.

In the technical means described above, the target substance of the present invention includes a wide range of substances as long as the substances carry out a gelation reaction with a predetermined reagent to produce gel particles. Examples of the target substance include an endotoxin and a β-D-glucan, and examples of the predetermined reagent in this case include a limulus reagent.

Further, the sample cell 1 may be fully constituted of a transmittable member, but the constitution thereof is not limited to the above constitution. Any constitution will do as long as at least a transmission portion is provided at the portion through which the light Bm passes.

Further, from the viewpoint of keeping a measurement condition constant, a preferred form is that the sample cell 1 is provided in a thermostatic chamber 8.

Besides, the stirring means 2 includes a wide range of means as long as the means provides a stirring action to the mixed solution W including the sample S and the solution containing the reagent R. A form in which means is built in and directly performs stirring may be included of course, and any form may be suitably selected from, for example, a form in which a stirring action is provided by air and a form in which a stirring action is provided by shaking.

Here, the degree of stirring by the stirring means 2 is required to be such that the mixed solution W including the sample S and the solution containing the reagent R in the sample cell 1 is disturbed from gelating as a whole.

In particular, from the viewpoint that stirring movement by the stirring means 2 may be conducted for sure, the sample cell 1 is preferably such that the stirring means 2 which is capable of stirring the mixed solution W including the sample S and the solution containing the reagent R is built in the cell container.

Still further, the coherent light source 3 is not limited to the laser light source delivering laser light as long as coherent light is delivered. For example, the coherent light source 3 may also be produced by passing monochromatic light such as light of a sodium lamp through a pin hole.

Further, any transmitted light detecting means will do as the transmitted light detecting means 4 as long as the transmitted light detecting means mainly detects the transmitted light that has transmitted through the sample S and the solution containing the reagent R out of light from the coherent light source 3. In this case, part of the scattered light scattered by gel particles may be detected as stray light by the transmitted light detecting means 4. However, as a detection output mostly includes a transmitted light component, the detection output may partially include a stray light component. Further, from the viewpoint of avoiding an influence by the stray light component, for example, a technique for removing the stray light component may be adopted, or the transmitted light fluctuation measuring means 5 may be used to correct the output.

Here, as the technique for removing the stray light component, a preferred form is that a scattered light removing means 7 is provided between the transmitted light detecting means 4 and the sample cell 1, the scattered light removing means 7 removing a component travelling toward the transmitted light detecting means 4 out of phase-shifted scattered light scattered by the gel particles. Examples of the scattered light removing means 7 include a polarized filter that allows only a transmitted light component to pass through by cutting off a scattered light component.

Besides, any transmitted light fluctuation measuring means will do as the transmitted light fluctuation measuring means 5 as long as the transmitted light fluctuation measuring means measures the fluctuation component of transmitted light based on the detection output of the transmitted light detecting means 4. Examples of the transmitted light fluctuation measuring means include a technique that applies a filtering procedure to the detection output while applying an averaging procedure or a smoothing procedure thereto.

Still further, the gel particle production determining means 6 includes a wide range of means which determines at least the production state of the gel particles in the mixed solution W, which leads to the timing of phase transition of the mixed solution W from a sol phase to a gel phase.

In addition, the phrase "determine the production state of gel particles" of course includes direct determination of information regarding the production state of gel particles, and also includes determination of information that can be determined based on the production state of gel particles (for example, quantified information on a target substance).

Here, the phrase "the production state of gel particles" widely includes the time point of the production start (emergence) of gel particles, a change in the production process of gel particles, the time point of the production finish of gel particles, and the production amount of gel particles. Thus, the phrase may herein include other matters, as long as the phrase includes at least the timing of phase transition of the mixed solution W from a sol phase to a gel phase.

In particular, in order that the time point of the production start of gel particles is determined, it is recommended that a changing point at which the fluctuation displacement of the transmitted light changes from a stable state to an unstable state be determined emerging timing of the gel particles, based on the result of measurement by the transmitted light fluctuation measuring means 5.

Still further, from the viewpoint of visually observing the result of measurement by the transmitted light fluctuation measuring means 5, it is preferred that there be provided a display means 9 for displaying the result of measurement by the transmitted light fluctuation measuring means 5.

Next, operation of the gel particle measuring apparatus illustrated in FIG. 1 is described.

First, a gelation reaction is schematically illustrated in FIG. 2(a).

In the figure, when a reagent R specifically reacting with a target substance St in a sample S is present, a phenomenon in which the target substance St specifically reacts with the reagent R takes place at a rate depending on the concentration of the target substance St in the sample S. In the process of the reaction, a given factor in the reagent R is activated by the stimulation of the target substance St, resulting in the activation of a given enzyme. Upon the activation, for example, a water-soluble protein may be converted to an insoluble protein through a decomposition reaction caused by the enzyme, resulting in emergence of a gel particle G.

Figure 3:
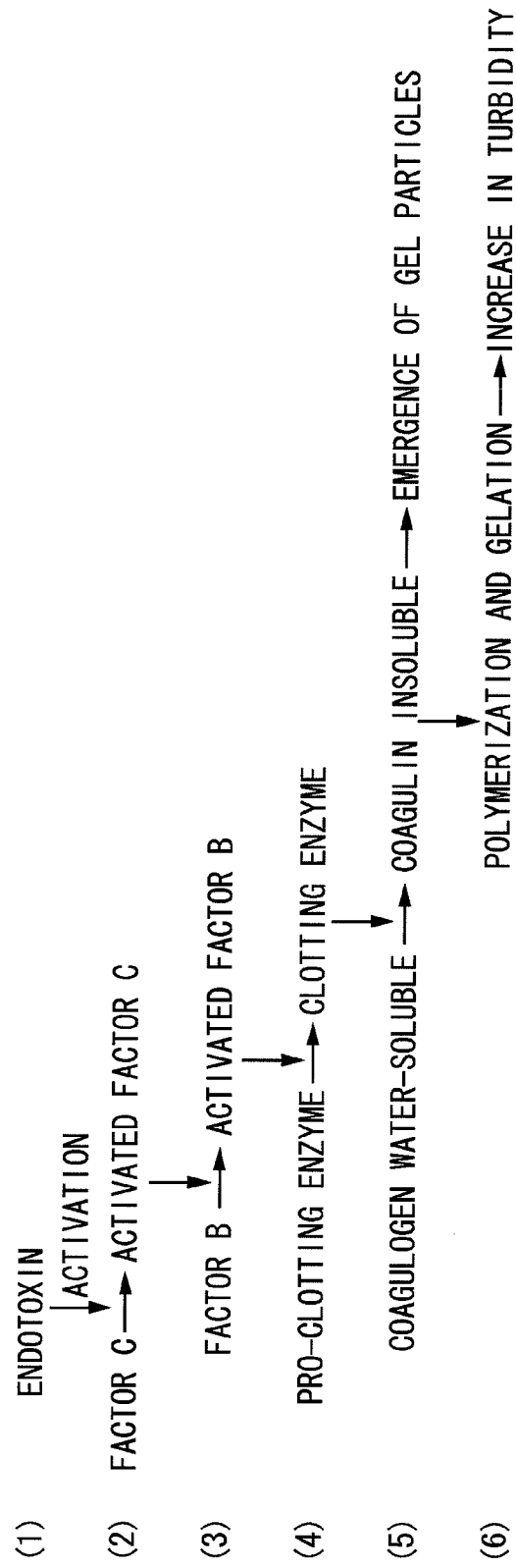
FIG. 3 is an explanatory diagram schematically illustrating a process of the gelation reaction of an endotoxin when a limulus reagent is used.

To be more specific, by taking an endotoxin for example, a process of the gelation reaction of the endotoxin is schematically illustrated in FIG. 3.

In the figure, after the stimulation of the endotoxin shown in (1) is delivered to a limulus reagent, Factor C is first activated into Activated Factor C as shown in (2). Next, the action of Activated Factor C causes the activation of Factor B, producing Activated Factor B as shown in (3). After that, the action of Activated Factor B causes the conversion of a pro-clotting enzyme to a clotting enzyme as shown in (4). As shown in (5), this clotting enzyme decomposes coagulogen (water-soluble protein), producing coagulin (insoluble protein). When gelation of the coagulin (insoluble protein) as a whole is prevented by stirring, a gel particle G of coagulin appears. When the whole is left to stand still, polymerization and gelation take place as shown in (6).

That is, in the case where the target substance St in the sample S is an endotoxin, when the stimulation of the endotoxin is delivered to the limulus reagent R while providing a constant stirring state to a mixed solution W prevents the gelation of the mixed solution W as a whole, the limulus reagent R can cause the production of the gel particles G of coagulin (insoluble protein) around the clotting enzyme. Thus, it is understood that after a gel particle G of coagulin (insoluble protein) is produced, a reaction process in which the gel particles G are subsequently produced follows.

Further, it was found that a rate at which the stimulation of the endotoxin was delivered to the limulus reagent R (limulus response rate) was dependent on an endotoxin concentration, and that as the endotoxin concentration was higher, the limulus response rate was higher, and the emerging timing of the gel particles G made of coagulin (insoluble protein) was earlier.

Thus, if changes in transmitted light are detected with high precision, the emerging timing of the gel particles G made of coagulin (insoluble protein) can be observed as the starting point of the production of the gel particles G. This is a fundamental of the measuring principle of the gel particle measuring apparatus according to this embodiment.

The measuring principle of the gel particle measuring apparatus described above is completely different from, for example, the measuring principle of the conventional gelation method or conventional turbidimetric time assay (the form in which in the reaction process by the limulus reagent R under a static condition, gelation finally occurs owing to the influence of an activated enzyme, and the gelated state is measured based on the turbidity).

Here, the measuring principle of the gel particle measuring apparatus is schematically illustrated in FIG. 2(b).

In the gel particle measuring apparatus of this embodiment, as illustrated in Step I in FIG. 2(b), when the mixed solution W including the sample S and the solution containing the reagent R is free of gel particles (corresponding to the case where the mixed solution W is in a sol phase), transmitted light $Bm_1$ from a coherent light source not shown is not shielded by the gel particles. Thus, the transmitted light intensity of the transmitted light $Bm_1$ is kept nearly constant (see $P_1$ of Step I in FIG. 2(c)).

Further, as illustrated in Step II in FIG. 2(b), when the production of the gel particles G starts in the mixed solution W including the sample S and the solution containing the reagent R (corresponding to the case where the phase transition of the mixed solution W from a sol phase to a gel phase starts), if the gel particles G of coagulin (insoluble protein) in the case of, for example, an endotoxin start to be produced, transmitted light $Bm_2$ from the coherent light source not shown is partially shielded by the presence of the produced gel particles G made of coagulin (insoluble protein). As a result, the transmitted light intensity of the transmitted light $Bm_2$ begins to change from a nearly constant level to an attenuating tendency (see $P_2$ of Step II in FIG. 2(c)).

After that, as illustrated in Step III in FIG. 2(b), when the production of the gel particles G gradually progresses in the mixed solution W including the sample S and the solution containing the reagent R, transmitted light $Bm_3$ from the coherent light source not shown is shielded by the presence of many gel particles G sequentially produced. As a result, the transmitted light intensity of the transmitted light $Bm_3$ begins to gradually attenuate from the changing point to attenuation $P_2$ (see $P_3$ of Step III in FIG. 2(c)).

In the embodiment described above, there is shown the form in which the production state of the gel particles, which leads to the timing of phase transition of the mixed solution from a sol phase to a gel phase, is at least determined, based on the fluctuation component of the transmitted light that transmits through the mixed solution W.

However, it was revealed that the above-mentioned action remarkably occurred in the transmitted light from the mixed solution W, and also occurred in scattered light excluding the transmitted light.

When the above point is taken into consideration, examples of the gel particle measuring apparatus according to the embodiment illustrated in FIG. 1 include a gel particle measuring apparatus for detecting a particle produced by subjecting a target substance in a sample S to a gelation reaction, the apparatus including: a sample cell 1 that has at least a transmission portion through which light transmits and that contains a sample S containing the target substance as a measuring object and a solution containing a reagent R for causing gelation of the target substance; stirring means 2 for stirring a mixed solution W including the sample S and the solution containing the reagent R in the sample cell 1 so as to inhibit gelation of the mixed solution W as a whole; a coherent light source 3 that is provided outside the transmission portion of the sample cell 1 and irradiates the mixed solution W including the sample S and the solution containing the reagent R in the sample cell 1 with coherent light; passing light detecting means (not shown) that is provided at a position outside the transmission portion of the sample cell 1, the position being different from a position at which the coherent light source 3 is provided, and that is used for detecting light which has passed through the mixed solution W including the sample S and the solution containing the reagent R in the sample cell 1; passing light fluctuation measuring means (not shown) for measuring a fluctuation component of the passing light based on the detection output of the passing light detecting means; and gel particle production determining means 6 for determining at least the production state of gel particles in the mixed solution W, which leads to the timing of phase transition of the mixed solution W from a sol phase to a gel phase, based on the result of measurement by the passing light fluctuation measuring means.

In this form, out of the passing light that passes through the mixed solution W in the sample cell 1, the passing light which is a detecting object by the passing light detecting means includes not only transmitted light but also scattered light.

Further, in this form, typical forms of the gel particle production determining means 6 include gel particle production determining means for determining a changing point at which the fluctuation displacement of the passing light changes from a stable state to an unstable state, as the emerging timing of the gel particles, based on the result of measurement of the passing light fluctuation measuring means.

Besides, as a preferred form out of forms in which the passing light detecting means detects the scattered light as the passing light, it is recommended that the coherent light source 3 irradiate the mixed solution W with coherent light so that the coherent light passes near the center of the sample cell 1, and the passing light detecting means detect the scattered light out of light from the coherent light source 3, which passes through the mixed solution W in the sample cell 1.

Here, the passing light detecting means may be installed at any position as long as the passing light detecting means detects the scattered light at the position. From the viewpoints that scattered light intensity can be secured sufficiently and installation is easily carried out, a preferred form is that the passing light detecting means is installed in a region opposite to that of the coherent light source 3 across the sample cell 1.

Still further, as a preferred form out of forms in which the passing light detecting means detects the transmitted light and the scattered light as the passing light, it is recommended that the coherent light source 3 irradiate the mixed solution W with coherent light so that the coherent light passes near the center of the sample cell 1, and the passing light detecting means detect the transmitted light and the scattered light out of light from the coherent light source 3, which passes through the mixed solution W in the sample cell 1.

Here, the passing light detecting means may be installed at any position as long as the passing light detecting means detects the transmitted light and the scattered light at the position. From the viewpoints that scattered light intensity can be secured sufficiently and installation is easily carried out, a preferred form is that the passing light detecting means is installed together with the transmitted light detecting means 4 in the region opposite to that of the coherent light source 3 across the sample cell 1.

Hereinafter, the present invention is described in more detail based on embodiments illustrated in the figures attached.

Embodiment 1

A gel particle measuring apparatus according to Embodiment 1 is, as illustrated in FIGS. 4(a) and 4(b), used for, for example, measuring the concentration of an endotoxin as a target substance in a sample S through a gelation reaction using a limulus reagent.

In the figures, Symbol 10 represents a sample cell integrally formed of, for example, a transparent resin material or a glass material, and the sample cell is used for containing a mixed solution W including the sample S containing the endotoxin and the limulus reagent R.

Here, in this embodiment, the sample cell 10 is formed of, for example, a tube with the upper portion open, having a circular shape in a cross-section, and having a bottom, and is structured so that the upper open portion is opened and closed, for example, by the opening and closing motion of an opening and closing lid. (not shown) on a measuring stage.

In addition, in this embodiment, the sample cell 10 is placed in a thermostatic chamber 15 so that the mixed solution W including the sample S and a solution containing the reagent R is placed under a constant thermostatic environment (for example, 37° C.), thereby keeping a measuring condition constant.

In addition, Symbol 20 represents a stirring device for stirring the mixed solution W in the sample cell 10, and is structured so that, for example, a constant stirring state is provided to the mixed solution W, to thereby disturb the mixed solution W as a whole from being gelated.

In particular, in this example, the stirring device 20 is provided with a stirrer bar 21 which is formed of a magnetic material and built in on the bottom wall in the sample cell 10 and a stirring-driving source (magnetic stirrer) 22 which is installed on the outer bottom wall of the sample cell 10 and causes the stirrer bar 21 to function its stirring force with a magnetic force.

Besides, Symbol 30 represents a laser light source which is installed on one side of the outer circular wall of the sample cell 10 and delivers coherent light, and Symbol 40 represents a transmitted light detector which is installed at a side opposite to that of the laser light source 30 across the sample cell 10 and detects transmitted light Bm from the laser light source 30. Optical parts such as a photodiode can be widely used for the transmitted light detector 40.

In this embodiment, coherent light Bm from the laser light source 30 is, as illustrated in FIG. 4(b), delivered along on a route that runs along the near-diameter line of the sample cell 10, and the diameter of the light is set to a value (for example, about 1 mm) sufficiently larger than the diameter (for example, about 0.5 to 20 μm) of each of the gel particles produced.

On the other hand, the transmitted light detector 40 has a detecting surface which is capable of detecting the light beam region of the transmitted light Bm from the laser light source 30. The detection accuracy of the transmitted light detector 40 is set to such an accuracy level that a change in the amount of the transmitted light caused by the presence or absence of one to several gel particles existing in the area through which the transmitted light Bm passes can be detected.

Besides, in this embodiment, a polarizing filter 50 is installed between the sample cell 10 and the transmitted light detector 40. The polarizing filter 50 removes stray light which is scattered light scattered by the gel particles G produced in the mixed solution W out of the light Bm from the laser light source 30 and is a component travelling toward the transmitted light detector 40. The principle of removing stray light by the polarizing filter 50 is such that a stray light component in a phase component excluding the phase of the transmitted light Bm is removed by taking advantage of the phenomenon in which when the coherent light Bm from the laser light source 30 is scattered by the gel particles G, the scattered light undergoes phase shifting.

Note that an optical part such as a collecting lens or a mirror may be arranged of course between the laser light source 30 and the sample cell 10 or between the transmitted light detector 40 and the sample cell 10 if the arrangement is necessary for determining a light path or the diameter of irradiating light.

Figure 5:
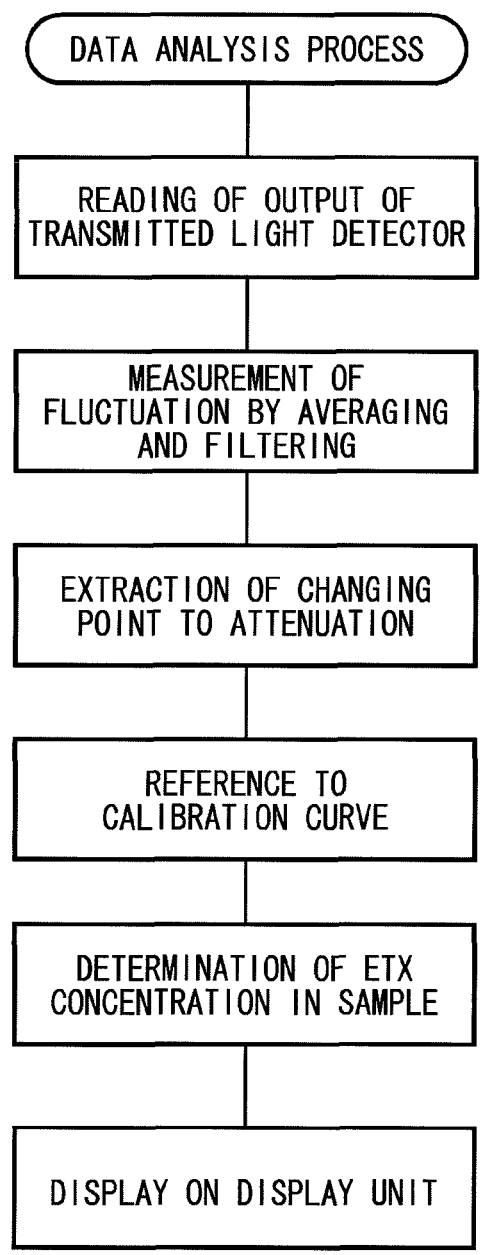
FIG. 5 is a flow chart illustrating one example of data analysis process by the gel particle measuring apparatus according to Embodiment 1.
Figure 9:
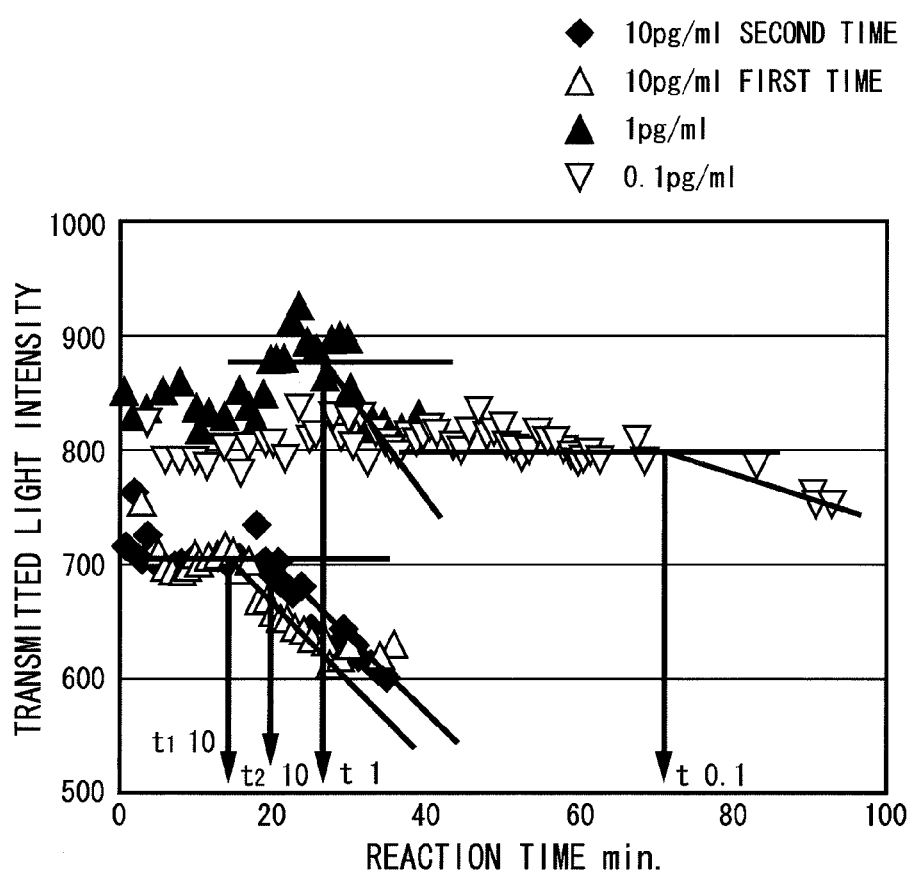
FIG. 9 is a graph illustrating results obtained by measuring a transmitted light intensity for each reaction time at various endotoxin concentrations (ETX concentrations) by using a gel particle measuring apparatus according to Example 1.

Symbol 60 represents a data analysis device which takes in a detection output from the transmitted light detector 40 and carries out such a data analysis process as illustrated in FIG. 5. Symbol 70 represents a display unit for displaying the results of the analysis performed with the data analysis device 60.

The data analysis device 60 is configured by a computer system including a CPU, a ROM, a RAM, an I/O interface, and the like. For example, a data analysis program illustrated in FIG. 5 is preliminarily installed in the ROM, and the data analysis program is executed with the CPU based on the detection output from the transmitted light detector 40.

Note that the detection output from the transmitted light detector 40 is, for example, subjected to current-voltage conversion in an amplifier not shown before subjected to AD conversion in an AD converter, and is taken into the data analysis device 60.

Next, operation of the gel particle measuring apparatus according to this embodiment is described.

In this embodiment, the sample S containing an endotoxin and a limulus reagent R are loaded into the sample cell 10 in the gel particle measuring apparatus illustrated in FIGS. 4(a) and 4(b), and then the opening and closing lid not shown on the measuring stage is closed and a start switch not shown is switched on, leading to the start of measurement sequence by the gel particle measuring apparatus.

The measurement sequence causes the stirring device 20 to stir the mixed solution W including the sample S and the limulus reagent R in the sample cell 10. Thus, the mixed solution W as a whole is disturbed from gelation.

Besides, the measurement sequence causes the following. That is, the light Bm is irradiated from the laser light source 30, the transmitted light Bm having passed through the mixed solution W in the sample cell 10 is detected with the transmitted light detector 40, and the detection output of the transmitted light detector 40 is taken into the data analysis device 60.

On the other hand, in the sample cell 10, the stimulation of the endotoxin is delivered to the limulus reagent R, a limulus response illustrated in FIG. 3 takes place, and the gel particles G are sequentially produced while the gelation of the mixed solution W as a whole is inhibited.

In this embodiment, the timing at which, for example, one gel particle G is produced in the area through which the light Bm from the laser light source 30 passes is taken as the starting point of the production of the gel particles G, and hence the timing is equivalent to the timing of the changing point to attenuation of the transmitted light.

In the reaction process described above, the data analysis device 60, for example, as illustrated in FIG. 5, reads the detection output from the transmitted light detector 40 as data of the amount of transmitted light (digital data), and then averaging and filtering processes are carried out to measure the fluctuation component in the data of the amount of transmitted light.

Next, the changing point to attenuation (corresponding to $P_2$ in FIG. 2) of the transmitted light is extracted based on the fluctuation component in the data of the amount of transmitted light, and the endotoxin concentration (ETX concentration) in the sample S is determined by referring to a preliminarily defined calibration curve. The result is displayed on the display unit 70.

The calibration curve in this example shows a relationship between the endotoxin concentration (ETX concentration) and the threshold of a time when the transmitted light reaches the changing point to attenuation. The endotoxin concentration (ETX concentration) is determined based on a relationship between the time taken for the transmitted light to reach the changing point to attenuation and the calibration curve. Further, the display unit 70 is switched to display data such as time-series data of the amount of transmitted light and time-series measurement data of the fluctuation component in the data of the amount of transmitted light, in addition to displaying the endotoxin concentration (ETX concentration).

Note that a preparation method for the calibration curve is shown with reference to a specific example in the examples described below.

As described above, in this embodiment, the gel particle measuring apparatus stirs the mixed solution W including the sample S and the limulus reagent R under a predetermined thermostatic environment, and detects that the transmitted light is partially shielded by the emergence of the gel particles G formed of coagulin particles produced in the mixed solution W and the amount of the transmitted light reduces, to thereby determine the starting time of the gelation.

In particular, in this example, in order to make the detection accuracy of the transmitted light detector 40 highly sensitive, laser light, which is coherent and intense light, is used. Besides, in order to detect a minute change, a change at low concentrations is detected by particularly using the phenomenon in which scattered stray light hits the gel particles G formed of coagulin particles to cause phase shifting. As the stray light component is removed by the polarizing filter 50, only the transmitted light component from the laser light source 30 enters the transmitted light detector 40, and hence a change in the transmitted light is accurately detected.

Varied Embodiment

In this embodiment, the sample cell 10 is structured so that the upper open portion is opened and closed, for example, with the opening and closing lid on the measuring stage. However, the structure of the sample cell 10 is not limited to the above. For example, the sample cell 10 may be structured so that the stirrer bar 21 and the limulus reagent R are preliminarily placed in a cell container and the upper open portion is sealed with a sealing member not shown. It is recommended that the sample cell 10 described above be supplied to users as an accessory of the gel particle measuring apparatus or as a measuring kit.

Further, as a method of introducing the sample S into the sample cell 10 in this form, there is exemplified a method in which a borer such as an injection needle is used to make a hole in the sealing member and the sample S is injected through the hole. Besides, in order to introduce the sample S easily, the sealing specification of the sealing member may be set so that the inside of the sample cell 10 is kept at a predetermined negative pressure level with respect to the atmospheric pressure.

Further, this embodiment shows a gel particle measuring apparatus for a sample cell 10 suitable for containing one specimen (sample S). Under the situation where simultaneous treatments of a plurality of specimens (samples) are required, it is recommended that, for example, a multi sample cell produced by integrating a plurality of sample cells be prepared, and there be disposed respective laser light sources 30 and respective transmitted light detectors 40 corresponding to the respective sample cells so that the plurality of specimens (samples) can be measured at the same time.

Besides, Embodiment 1 discloses a gel particle measuring apparatus in which a substance as a measuring object is an endotoxin, but the substance as a measuring object is not limited to the endotoxin. For example, while the same measuring hardware is used and the same or similar limulus reagent is used, the substance as a measuring object may be changed to a β-D-glucan.

In addition, it is also possible to sharply detect a reaction of a substance with respect to produce particles or cause the polymerization of particles.

Embodiment 2

FIGS. 6(a) and 6(b) illustrate the main section of a gel particle measuring apparatus according to Embodiment 2.

In the figures, the gel particle measuring apparatus according to Embodiment 2 contains a sample S containing an endotoxin and a *limulus* reagent R in a sample cell 10, irradiates the inside of a mixed solution W of the sample S and the *limulus* reagent R with light Bm' from a laser light source 30 while the mixed solution W is stirred with a stirring device 20 (stirrer bar 21 and stirring-driving source 22). Then, the gel particle measuring apparatus partially detects, with a scattered light detector 140, the scattered light which is laterally scattered by gel particles G produced by an *limulus* response, takes a detection output of the scattered light detector 140 into a data analysis device 60, and determines the time of the initial production of the gel particles G by arithmetic processing.

The gel particle measuring apparatus according to Embodiment 2 can measure only part of the scattered light because the proportion of the scattered light is originally small compared with that of transmitted light, and hence it is necessary to suppress the attenuation of the scattered light as much as possible. Thus, a strict optical circuit is required in Embodiment 2 in order to prevent the attenuation of the scattered light. As illustrated in FIG. 6(b), the laser light source 30 and the scattered light detector 140 must be installed so that an incident angle and a scattered light reflection angle are provided in an orthogonal positional relationship on the surface of the mixed solution G in the sample cell 10, to thereby measure the scattered light. Thus, it is also required for the sample cell 10 to adopt a special container structure which has a smaller thickness k causing less attenuation, or it is required to carefully set the installation accuracy of the laser light source 30 and the scattered light detector 140 to an extremely high level.

In contrast, in Embodiment 1, in addition to the fact that a large amount of a transmitted light component can be originally secured, a tough container having a large thickness can be used without adopting a particularly special structure as the container structure of the sample cell 10. Further, the laser light source 30 and the transmitted light detector 40 maybe installed with respect to the sample cell 10 at positions opposed with each other on a straight line along the near-diameter direction of the sample cell 10, and hence the installation accuracy of the sample cell 10 involved in its exchange can be inaccurate to a certain extent.

Embodiment 3

FIGS. 7(a) and 7(b) illustrate the main section of a gel particle measuring apparatus according to Embodiment 3.

In the figures, the gel particle measuring apparatus according to Embodiment 3 contains a sample S containing an endotoxin and a *limulus* reagent R in a sample cell 10, irradiates the inside of a mixed solution W of the sample S and the *limulus* reagent R with light Bm from a laser light source 30 so that the light Bm passes near the center of the sample cell 10 while the mixed solution W is stirred with a stirring device 20 (stirrer bar 21 and stirring-driving source 22). Then, the gel particle measuring apparatus partially detects, with a scattered light detector 140, scattered light which is transmitted and scattered by gel particles G produced by an *limulus* response toward the side opposite to that of the laser light source 30 across the sample cell 10, takes a detection output of the scattered light detector 140 into a data analysis device 60, and determines the time of the initial production of the gel particles G by arithmetic processing.

In this form, if the gel particles G are produced when the phase transition of the mixed solution W in the sample cell 10 takes place from a sol phase to a gel phase, the scattered light detector 140 partially detects the scattered light (precisely, light scattered in different directions from the traveling direction of transmitted light) which is transmitted and scattered by the presence of the gel particles G. Here, it is recommended that the sensitivity of the scattered light detector 140 be selectively set to the sensitivity at which the level of the scattered light scattering when the production of the gel particles starts can be sensed, because the scattered light is not generated when the gel particles are not produced, but is generated owing to the production of the gel particles.

Then, the output of the scattered light detected by the scattered light detector 140 is taken into the data analysis device 60, the initial changing point in the output of the scattered light is determined based on the fluctuation component of the scattered light, and the time of the initial changing point is calculated as the time of the initial production of the gel particles G.

Further, at least one scattered light detector 140 is enough in this form, but the number of the scattered light detectors 140 may be suitably selected. For example, a plurality of scattered light detectors 140 may be installed to average a detection output, or to use one of the plurality of scattered light detectors 140 for determining the time of the initial production of the gel particles G and to use other scattered light detectors 140 for determining other production states of the gel particles G.

Note that, in this embodiment, the scattered light detector 140 is, as illustrated in FIG. 7(b) with solid lines, installed at a side opposite to that of the laser light source 30 across the sample cell 10. However, as illustrated in FIG. 7(b) with virtual lines, a scattered light detector 140' may be, for example, installed at a site which is dislocated by about 90° with respect to the position of the laser light source 30 in the circumference of the sample cell 10, to thereby detect, with the scattered light detector 140', the scattered light laterally scattered by the gel particles G in the mixed solution W out of light Bm from the laser light source 30. However, the sensitivity of the scattered light detector 140' is preferably higher compared with that of the scattered light detector 140, because the component of the laterally scattered light is smaller in amount compared with the component of the transmitted, scattered light shown with the solid lines in FIG. 7(b).

Embodiment 4

FIGS. 8(a) and 8(b) illustrate the main section of a gel particle measuring apparatus according to Embodiment 4.

In the figures, the gel particle measuring apparatus according to Embodiment 4 contains a sample S containing an endotoxin and a *limulus* reagent R in a sample cell 10, irradiates the inside of a mixed solution W of the sample S and the *limulus* reagent R with light Bm from a laser light source 30 so that the light Bm passes near the center of the sample cell 10 while the mixed solution W is stirred with a stirring device 20 (stirrer bar 21 and stirring-driving source 22). Then, the gel particle measuring apparatus, while partially detecting, with a transmitted light detector 40, transmitted light which transmits through gel particles G produced by an *limulus* response, out of passing light which is directed by the gel particles G toward the side opposite to that of the laser light source 30 across the sample cell 10, partially detects the scattered light which is transmitted and scattered differently from transmitted light by the gel particles G, with a scattered light detector 140, takes the detection outputs of the respective light detectors 40 and 140 into a data analysis device 60, and determines the time of the initial production of the gel particles G by arithmetic processing.

In this form, in the data analysis device 60, the detection outputs from the respective light detectors 40 and 140 may be calculated at time course, or at least one of the detection outputs may be converted, for example, to a parameter (such as turbidity) changing based on the transmitted light intensity or the scattered light intensity, followed by calculation.

Further, in this form, one laser light source 30 is enough, and installation of at least one each of the detectors 40 and 140 is enough. If necessary, a plurality of each of the detectors 40 and 140 may be installed.

When the gel particle measuring apparatus in the form described above is used, the transmitted light detector 40 detects the fluctuation component of the transmitted light, and on the other hand, the scattered light detector 140 detects the fluctuation component of the scattered light. Thus, the data analysis device 60 can determine the time of the initial production of the gel particles G in the mixed solution W in the sample cell 10, based on the fluctuation component of the transmitted light or scattered light from each of the light detectors 40 and 140. Further, the data analysis device 60 can determine the time of the initial production of the gel particles G more precisely by combining the both data.

Note that this form is not limited to the form in which the both light detectors 40 and 140 are used to determine the time of the initial production of the gel particles G. One of the light detectors 40 and 140 may be used to determine the time of the initial production of the gel particles G, and the other of the light detectors 140 and 40 may be used to determine the production state of the gel particles G excluding the time of the initial production of the gel particles G. Further, it is a matter of course that in place of the scattered light detector 140 for detecting scattered light, a scattered light detector 140' for detecting scattered light laterally scattered may be used as in the case of Embodiment 3.

EXAMPLES

Example 1

This example is a more specific example of the gel particle measuring apparatus according to Embodiment 1.

Here, the conditions of Example 1 are described below.
Laser light source 30: red light or green light
Transmitted light detector 40: photodiode
Number of rotations of stirrer bar 21: 1000 rpm
Thermostatic condition: 37° C.

In this example, for each of limulus reagents to which samples having various endotoxin concentrations (10, 1, and 0.1 pg/ml) were added, the gel particle measuring apparatus was used to investigate a change in the transmitted light intensity.

FIG. 7 is a graph prepared by plotting the values of the transmitted light intensity at time course for each of the concentrations of 10 pg/ml in two investigations, 1 pg/ml, and 0.1 pg/ml.

In the figure, any of the changes in the transmitted light intensities for respective conditions shows the tendency that the portion kept at a nearly constant level attenuates and declines after a certain time passes. The changing point to attenuation of each of the transmitted light intensities corresponds to the starting point of the production of gel particles (starting time of gelation), and is estimated to mean the reduction of light in amount owing to the starting time of gelation.

In order to determine the starting time of gelation, in this example, in the graph of FIG. 7, there was manually determined the intersection point between a straight line obtained by approximating the portion in which the transmitted light intensity is constant and a straight line obtained by approximating the changing portion in which the transmitted light intensity is attenuating and declining, to thereby determine each of the starting times of gelation (reaction times) $t_1(10)$, $t_2(10)$, $t(1)$, and $t(0.1)$.

In this example, the starting times of gelation were as follows:

| | |
|---|---|
| 10 pg/ml: | $t_1(10)$ = 16 (min.) |
| | $t_2(10)$ = 19 (min.) |
| 1 pg/ml: | $t(1)$ = 28 (min.) |
| 0.1 pg/ml: | $t(0.1)$ = 70 (min.). |

For comparison, an endotoxin kit (gelation reaction measuring apparatus) manufactured by Wako Pure Chemical Industries, Ltd. and adopting a turbidimetric time assay was used, and endotoxin concentrations and gelation times were investigated. The following results were provided.

| Endotoxin concentration (pg/ml) | Gelation time (min.) |
|---|---|
| 0.1 | 123.7 |
| 0.5 | 56.3 |
| 1.0 | 41.8 |
| 10.0 | 18.0 |

Figure 10:
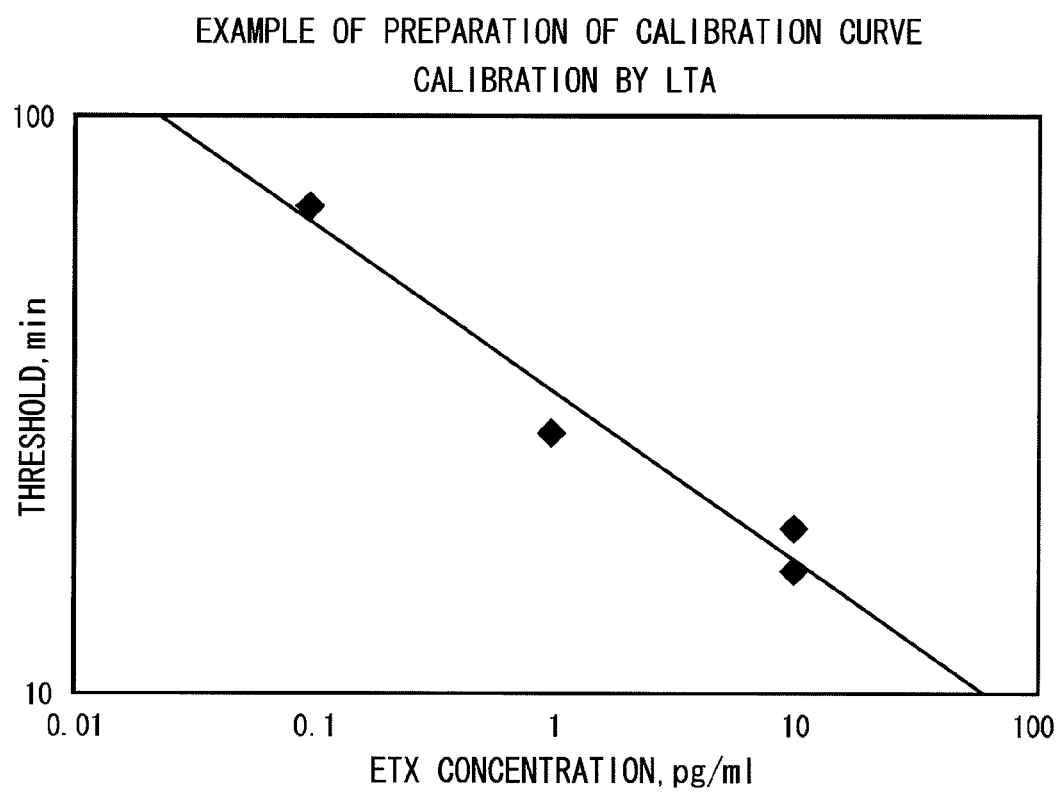
FIG. 10 is an explanatory diagram illustrating an example of preparing a calibration curve by using the graph illustrated in FIG. 9.

Moreover, in this example, the values of the starting times of gelation $t_1(10)$, $t_2(10)$, $t(1)$, and $t(0.1)$, which were obtained from the graph of FIG. 7, were used to prepare a calibration curve in FIG. 10.

In the calibration curve of this example, the ETX concentration (logarithmically converted) as the endotoxin concentration is taken in the X-axis and the staring time of gelation (logarithmically converted) is taken in the Y-axis. Then, a linear relationship results, and a high correlation showing a correlation coefficient of 0.9804 is exhibited, which proves that the calibration curve is useful.

Example 2

This example is a specific example of the gel particle measuring apparatus according to Embodiment 4.

Here, the conditions of Example 2 are described below.
Laser light source 30: blue color and 20 mW
Transmitted light detector 40: photodiode
Scattered light detector 140: photodiode
Number of rotations of stirrer bar 21: 1000 rpm
Thermostatic condition: 37° C.

In this example, for a *limulus* reagent to which a sample having a predetermined endotoxin concentration (10 pg/ml) was added, each of the changes in the transmitted light intensity and scattered light intensity was investigated twice. Note that in this example, a calculated result based on the turbidity is displayed as a parameter corresponding to the transmitted light intensity, and a calculated result based on the degree of the scattering is displayed as a parameter corresponding to the scattered light intensity.

FIG. 11(*a*) is a graph obtained by plotting the turbidity at time course corresponding to the transmitted light intensity in the case where the sample having an endotoxin concentration of 10 pg/ml was added to the *limulus* reagent.

FIG. 11(*b*) is a graph obtained by plotting the degree of the scattering at time course corresponding to the scattered light intensity in the case where the sample having an endotoxin concentration of 10 pg/ml was added to the *limulus* reagent.

According to FIG. 11(*a*), a change in each of the turbidities corresponding to the transmitted light intensities shows the tendency that the portion kept at a nearly constant level attenuates and declines after a certain time passes. The changing point to attenuation of each of the turbidities corresponding to the transmitted light intensities corresponds to the starting point of the production of gel particles (starting time of gelation), and is estimated to mean a reduction in turbidity involved in the reduction of light in amount owing to the starting time of gelation.

On the other hand, according to FIG. 11(*b*), each of the degrees of the scattering corresponding to the scattered light intensities shows the tendency that the portion kept at a nearly constant level increases and rises after a certain time passes. The changing point to increase of each of the degrees of the scattering corresponds to the starting point of the production of gel particles (starting time of gelation), and is estimated to mean an increase in the degree of the scattering involved in the scattering owing to the starting time of gelation.

Note that the changing point to increase of each of the degrees of the scattering corresponding to the scattered light intensities illustrated in FIG. 11(*b*) is a little bit behind the changing point to attenuation of each of the turbidities corresponding to the transmitted light intensities as illustrated in FIG. 11(*a*). This is probably because of the difference in the arrival time of reaction between the transmitted light and the scattered light arriving at the light detectors 40 and 140, respectively.

Example 3

This example is a specific example of the gel particle measuring apparatus according to Embodiment 4 in the similar manner to that in Example 2.

Here, the conditions of Example 3 are nearly the same as those of Example 2, but a blue 40 mW diode is used as the laser light source 30 instead.

In this example, for each of *limulus* reagents to which samples having various endotoxin concentrations (10, 1, 0.1, and 0.001 pg/ml) were added, the gel particle measuring apparatus was used to investigate changes in the turbidity corresponding to the transmitted light intensity and changes in the degree of the scattering corresponding to the scattered light intensity.

FIG. 12(*a*) is a graph obtained by plotting each of the degrees of the scattering at time course corresponding to the transmitted light intensities in the case where the samples having various endotoxin concentrations were added to the *limulus* reagents. FIG. 12(*b*) is a graph obtained by plotting each of the turbidities at time course corresponding to the scattered light intensities in the case where the samples having various endotoxin concentrations were added to the *limulus* reagents.

Here, according to FIG. 12(*a*), a change in each of the turbidities corresponding to the transmitted light intensities for each of the samples having respective endotoxin concentrations shows the tendency that the portion kept at a nearly constant level attenuates and declines after a certain time passes. The changing point to attenuation of each of the turbidities corresponding to the transmitted light intensities corresponds to the starting point of the production of gel particles (starting time of gelation), and is estimated to mean a reduction in turbidity involved in the reduction of light in amount owing to the starting time of gelation. It is understood that the changing point to attenuation of each of the turbidities corresponding to the respective transmitted light intensities (starting points of the production of gel particles) is earlier as the endotoxin concentration is higher.

On the other hand, according to FIG. 11(b), each of the degrees of the scattering corresponding to the scattered light intensities for each of the samples having respective endotoxin concentrations shows the tendency that the portion kept at a nearly constant level increases and rises after a certain time passes. The changing point to increase of each of the degrees of the scattering corresponds to the starting point of the production of gel particles (starting time of gelation), and is estimated to mean an increase in the degree of the scattering involved in the scattering owing to the starting time of gelation. It is understood that the changing point to increase of each of the degrees of the scattering (starting points of the production of gel particles) is earlier as the endotoxin concentration is higher.

Then, it is possible to prepare a calibration curve from those results by using the values of the starting times of gelation, which are the starting points of gelation, in nearly the same manner as that shown in Example 1. In this case, if the starting times of gelation are determined by taking the fluctuation components of both the transmitted light and scattered light into consideration, disturbance caused by noise or the like can be removed. As a result, the starting times of gelation are determined more accurately.

Example 4

This example is a specific example of the gel particle measuring apparatus according to Embodiment 4 in the similar manner to that in Example 3. This example is different from Example 3 in the use of a 40 mW red diode as the laser light source. Note that the conditions of this example are nearly the same as those of Example 3.

In this example, as in Example 3, for each of *limulus* reagents to which samples having various endotoxin concentrations (10, 1, 0.1, and 0.001 pg/ml) were added, the gel particle measuring apparatus was used to investigate a change in the turbidity corresponding to the transmitted light intensity and a change in the degree of the scattering corresponding to the scattered light intensity.

FIGS. 13(a) and 13(b) illustrate the results.

FIG. 13(a) is a graph obtained by plotting each of the turbidities at time course corresponding to the transmitted light intensities in the case where the samples having various endotoxin concentrations were added to the *limulus* reagents.

On the other hand, FIG. 12(b) is a graph obtained by plotting each of the degrees of the scattering at time course corresponding to the scattered light intensities in the case where the samples having various endotoxin concentrations were added to the *limulus* reagents.

According to the figures, nearly the same results as those in Example 3 were obtained though a different laser light source 30 was used. As a result, it was confirmed that the results could be used for preparing the above-mentioned calibration curve or the like.

Example 5

This example is a more specific example of the gel particle measuring apparatus (a form in which the scattered light detector 140' is used) according to Embodiment 3.

In this example, nearly the same conditions as those in Example 2 were used and, for a *limulus* reagent to which a sample having a predetermined endotoxin concentration (10 pg/ml) was added, a change in laterally scattered light intensity was investigated once.

Figure 14:
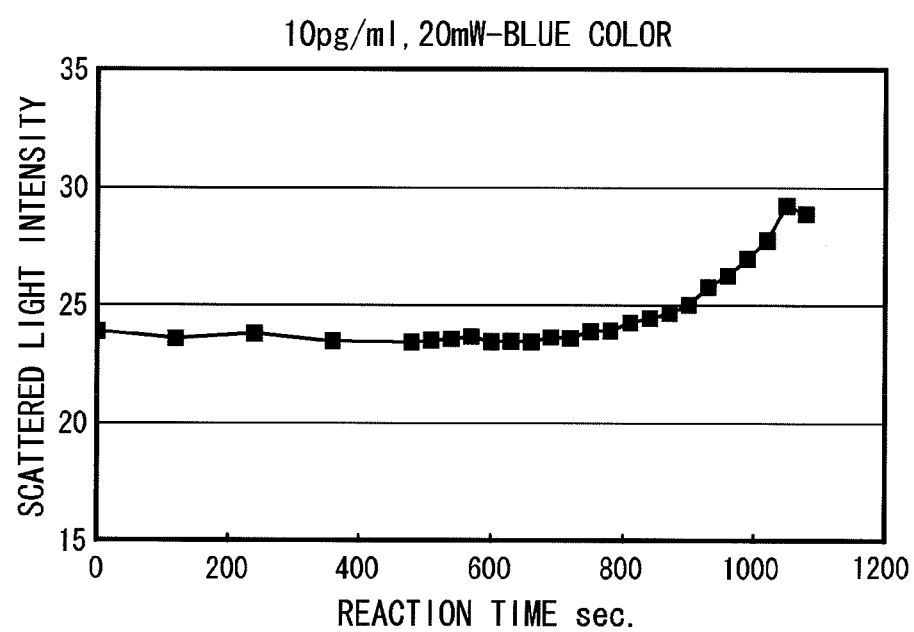
FIG. 14 is a graph illustrating results obtained by measuring once a scattered light intensity for each reaction time at a predetermined endotoxin concentration (ETX concentration) by using a gel particle measuring apparatus according to Example 5.

FIG. 14 illustrates the result.

FIG. 14 is a graph obtained by plotting the laterally scattered light intensity at time course in the case where the sample having an endotoxin concentration of 10 pg/ml was added to the *limulus* reagent.

According to the figure, the laterally scattered light intensity also shows the tendency that the portion kept at a nearly constant level increases and rises after a certain time passes. The changing point to increase of the scattered light intensity corresponds to the starting point of the production of gel particles (starting time of gelation), and is estimated to mean an increase in light intensity involved in the scattering owing to the starting time of gelation.

INDUSTRIAL APPLICABILITY

The present invention is widely applied to a measuring apparatus the measuring object of which is a target substance which can produce gel particles through a gelation reaction or a reaction process where polymerization of existing particles takes place, the measuring apparatus including a gel particle measuring apparatus the measuring object of which is an endotoxin, a β-D-glucan, or the like with the use of a *limulus* reagent.

The invention claimed is:
1. A gel particle measuring apparatus for detecting particles produced from a target substance in a sample by a gelation reaction, the apparatus comprising:
 a sample cell that has at least a transmission portion through which light transmits from one side to another side and that accommodates a sample containing a target substance as a measuring object and a solution containing a reagent causing gelation of the target substance to produce gel particles;
 a stirring device for stirring a mixed solution comprising the sample and the solution containing the reagent in the sample cell continuously so as to disturb gelation of the mixed solution as a whole;
 a coherent light source that is provided outside the transmission portion of the sample cell and irradiates the continuously mixed solution comprising the sample and the solution containing the reagent in the sample cell with coherent light;
 a transmitted light detecting device that is provided at a position outside the transmission portion of the sample cell and on an opposite side of the coherent light source and that is used for detecting transmitted light through the continuously mixed solution comprising the sample and the solution containing the reagent in the sample cell;
 a transmitted light fluctuation measuring device for measuring a fluctuation component of the transmitted light based on a detection output of the transmitted light detecting device; and
 a gel particle production determining device for determining at least a production state of gel particles in the continuously mixed solution, which corresponds to timing of phase transition of the mixed solution from a sol phase to a gel phase, and which includes the emerging time of the gel particles which is the starting point of the production of the gel particles, based on a result of measurement of the transmitted light fluctuation measuring device, wherein the gel particles appear when gelation of the continuously mixed solution as a whole is disturbed by said stirring device.

2. A gel particle measuring apparatus according to claim 1, further comprising scattered light removing device for removing a component travelling toward the transmitted light detecting device out of phase-shifted scattered light scattered by gel particles, between the transmitted light detecting device and the sample cell.

3. A gel particle measuring apparatus according to claim 1 or 2, wherein the gel particle production determining device comprises a unit for determining a changing point, at which a fluctuation displacement of the transmitted light changes from a stable state to an unstable state, as emerging timing of the gel particles, based on the result of measurement of the transmitted light fluctuation detecting device.

4. A gel particle measuring apparatus according to claim 1, wherein the coherent light source comprises a laser light source.

5. A gel particle measuring apparatus according to claim 1, wherein the sample cell comprises, in a cell container, the stirring device with which the sample and the solution containing the reagent can be directly stirred.

6. A gel particle measuring apparatus according to claim 1, wherein the sample cell is provided in a thermostatic chamber.

7. A gel particle measuring apparatus according to claim 1, further comprising display device for displaying a result of determination by the gel particle production determining device.

8. A gel particle measuring apparatus according to claim 1, wherein the gel particle production determining device is adapted to quantify the target substance in the sample based on the production state of the gel particles.

9. A gel particle measuring apparatus for detecting particles produced from a target substance in a sample by a gelation reaction, the apparatus comprising:
   a sample cell that has at least a transmission portion through which light transmits and that accommodates a sample containing a target substance as a measuring object and a solution containing a reagent causing gelation of the target substance to produce gel particles;
   a stirring device for stirring a mixed solution comprising the sample and the solution containing the reagent in the sample cell continuously so as to disturb gelation of the mixed solution as a whole;
   a coherent light source that is provided outside the transmission portion of the sample cell and irradiates the continuously mixed solution comprising the sample and the solution containing the reagent in the sample cell with coherent light;
   a passed light detecting device that is provided at a position outside the transmission portion of the sample cell, the position being different from a position at which the coherent light source is provided, and that is used for detecting passed light, which is light that has passed through the continuously mixed solution comprising the sample and the solution containing the reagent in the sample cell;
   a passed light fluctuation measuring device for detecting a fluctuation component of the passed light based on a detection output of the passed light detecting device; and
   a gel particle production determining device for determining at least a production state of gel particles in the continuously mixed solution, which leads to timing of phase transition of the mixed solution from a sol phase to a gel phase, and which includes the emerging time of the gel particles which is the starting point of the production of the gel particles, based on a result of measurement of the passed light fluctuation detecting device,
   wherein the gel particles appear when gelation of the continuously mixed solution as a whole is disturbed by said stirring device.

10. A gel particle measuring apparatus according to claim 9, wherein the gel particle production determining device is adapted to determine a changing point, at which a fluctuation displacement of the passed light changes from a stable state to an unstable state, as emerging timing of the gel particles, based on the result of measurement of the passed light fluctuation detecting device.

11. A gel particle measuring apparatus according to claim 9, wherein
   the coherent light source irradiates the mixed solution with coherent light so that the coherent light passes near a center of the sample cell, and
   the passed light detecting device comprises a unit for detecting scattered light out of light from the coherent light source, the light passing through the mixed solution in the sample cell.

12. A gel particle measuring apparatus according to claim 9, wherein
   the coherent light source irradiates the continuously mixed solution with coherent light so that the coherent light passes near the center of the sample cell, and
   the passed light detecting device is adapted to detect transmitted light and the scattered light out of the light from the coherent light source, the light passing through the continuously mixed solution in the sample cell.

13. A gel particle measuring apparatus according to claim 9, wherein the target substance as the measuring object comprises an endotoxin and the reagent for gelating the endotoxin comprises a limulus reagent.

* * * * *